(12) United States Patent
Vinson et al.

(10) Patent No.: US 8,487,082 B2
(45) Date of Patent: Jul. 16, 2013

(54) SYNTHETIC SCFV ANALOGUE TO THE 6313/G2 (ANTI ANGIOTENSIN II TYPE 1 RECEPTOR) MONOCLONAL ANTIBODY VARIABLE REGIONS

(75) Inventors: Gavin Paul Vinson, London (GB); Stewart Barker, London (GB); John Richard Puddefoot, London (GB)

(73) Assignee: Queen Mary & Westfield College, London (GB)

( * ) Notice: Subject to any disclaimer, the term of this patent is extended or adjusted under 35 U.S.C. 154(b) by 0 days.

(21) Appl. No.: 12/867,911

(22) PCT Filed: Feb. 18, 2009

(86) PCT No.: PCT/GB2009/000443
§ 371 (c)(1),
(2), (4) Date: Dec. 7, 2010

(87) PCT Pub. No.: WO2009/103969
PCT Pub. Date: Aug. 27, 2009

(65) Prior Publication Data
US 2011/0081350 A1    Apr. 7, 2011

(30) Foreign Application Priority Data
Feb. 18, 2008  (GB) .................... 0802931.6

(51) Int. Cl.
*C07K 16/00*    (2006.01)
*A61K 39/395*   (2006.01)

(52) U.S. Cl.
USPC ..................... 530/387.1; 424/130.1

(58) Field of Classification Search
None
See application file for complete search history.

(56) References Cited

U.S. PATENT DOCUMENTS

| 6,063,620 | A | 5/2000 | Vinson et al. | |
| 2006/0034839 | A1* | 2/2006 | Barker et al. | 424/143.1 |

FOREIGN PATENT DOCUMENTS

| CA | 2093495 A | 4/1993 |
| CN | 1141000 | 1/1997 |
| WO | 95/09186 | 4/1995 |
| WO | 95/12410 A1 | 5/1995 |
| WO | 95/09186 | 4/1999 |
| WO | 02061087 A2 | 8/2002 |
| WO | 2004/018519 | 3/2004 |
| WO | 2004018519 | 3/2004 |

OTHER PUBLICATIONS

Muscella et al , J End 155:587-593, 1997.*
Redondo-Muller et al , Endocrine-Related Cancer 15:277-288, Mar. 1, 2008.*
Sequence search result—Vinson, 2010.
Sequence search result—Burmer, 2010.
Tamarat, R., et al., Angiotensin II angiogenic effect in vivo involves vascular endothelial growth factor- and inflammation-related pathways, Lab Invest. Jun. 2002;82(6):747-56.
Humphries, M. J., et al., Conjugation of synthetic peptides to carrier proteins for cell adhesion studies, J. of Tissue Culture Methods, 1994;16:239-42.
Fujimoto, Y., et al., Angiotensin II type 1 receptor expression in human pancreatic cancer and growth inhibition by angiotensin II type 1 receptor antagonist, FEBS Lett. Apr. 27, 2001;495(3):197-200.
Ezzell, C., Cancer "Vaccines": An Idea Whose Time as Come?, J. NIH Res, 1995;7:46-49.
Spitler, L. E., Cancer Vaccines: The Interferon Analogy, Cancer Biotherapy, 1995;10:1-3.
Boon, T., Toward a Genetic Analysis of Tumor Rejection Antigens, Adv Can Res, 1992;58:177-210.
De Gruijl, T. D., et al., Cancer vaccine strategies get bigger and better, Nat Med. Oct. 1999;5(10):1124-5.
Ngo, J. T., et al., Computational Complexity, Protein Structure Prediction, and the Levinthal Paradox, in The Protein Folding Problem and Tertiary Structure Prediction, Merz, et al., (ed.), Birkhauser, Boston, MA 1994:433 and 492-495.
Burgess, W. H., et al., Possible dissociation of the heparin-binding and mitogenic activities of heparin-binding (acidic fibroblast) growth factor-1 from its receptor-binding activities by site-directed mutagenesis of a single lysine residue, J Cell Biol. Nov. 1990;111(5 Pt 1):2129-38.
Lazar, E., et al., Transforming growth factor alpha: mutation of aspartic acid 47 and leucine 48 results in different biological activities, Mol Cell Biol. Mar. 1988;8(3):1247-52.
Coleman, P. M., Effects of amino acid sequence changes on antibody-antigen interactions, Research in Immunology, 1994;145(1):33-6.
Abaza, M. S., et al., Effects of amino acid substitutions outside an antigenic site on protein binding to monoclonal antibodies of predetermined specificity obtained by peptide immunization: demonstration with region 94-100 (ant

OTHER PUBLICATIONS

Barker, S., et al., A monoclonal antibody to a conserved sequence in the extracellular domain recognizes the angiotensin II AT1 receptor in mammalian target tissues, J Mol Endocrinol. Oct. 1993;11(2):241-5.

Cheng, H. F., et al., Young SHR express increased type 1 angiotensin II receptors in renal proximal tubule, Am J Physiol. Jan. 1998;274(1 Pt 2):F10-7.

De Paepe, B., et al., Growth stimulatory angiotensin II type-1 receptor is upregulated in breast hyperplasia and in situ carcinoma but not in invasive carcinoma, Histochem Cell Biol. Sep. 2001;116(3):247-54.

Harrison-Bernard, L. M., et al., Immunohistochemical localization of ANG II AT1 receptor in adult rat kidney using a monoclonal antibody, Am J Physiol. Jul. 1997;273(1 Pt 2):F170-7.

Inwang, E. R., et al., Angiotensin II type 1 receptor expression in human breast tissues, Br J Cancer. 1997;75 (9):1279-83.

Kapas, S., et al., Internalization of the type I angiotensin II receptor (AT1) is required for protein kinase C activation but not for inositol trisphosphate release in the angiotensin II stimulated rat adrenal zona glomerulosa cell, Biochem Biophys Res Commun. Nov. 15, 1994;204(3):1292-8.

Ling, S. et al., Matrix-dependent gene expressio of Egr-1 and PDGF a regulate angiotensin II-induced proliferation in human vascular smooth muscle cells., Hypertension, 1999;34:1141-46.

Marsigliante, S., et al., AT1 angiotensin II receptor subtype in the human larynx and squamous laryngeal carcinoma, Cancer Lett. Dec. 20, 1996;110(1-2):19-27.

Murphy, T. J., et al., Isolation of a cDNA encoding the vascular type-1 angiotensin II receptor, Nature. May 16, 1991;351(6323):233-6.

Richards, E. M., et al., Inhibition of central angiotensin responses by angiotensin type-1 receptor antibody, Hypertension. Jun. 1993;21(6 Pt 2):1062-5.

Tahmasebi, M., et al., Transcription of the prorenin gene in normal and diseased breast, Eur J Cancer. Oct. 1998;34(11):1777-82.

Touyz, R. M., et al., Angiotensin II stimulates DNA and protein synthesis in vascular smooth muscle cells from human arteries: role of extracellular signal-regulated kinases, J Hypertens. Jul. 1999;17(7):907-16.

Vinson, G. P., et al., Internalisation of the type I angiotensin II receptor (AT1) and angiotensin II function in the rat adrenal zona glomerulosa cell, J Endocrinol. May 1994;141(2):R5-9.

Yang, H., et al., Involvement of MAP kinase in angiotensin II-induced phosphorylation and intracellular targeting of neuronal AT1 receptors, J Neurosci. Mar. 1, 1997;17(5):1660-9.

Yang, B. C., et al., Increased angiotensin II type 1 receptor expression in hypercholesterolemic atherosclerosis in rabbits, Arterioscler Thromb Vasc Biol. Sep. 1998;18(9):1433-9.

ISR dated Apr. 21, 2004 for International Application No. PCT/GB03/03758.

Non-final Office Action dated Dec. 4, 2008 in co-pending U.S. Appl. No. 10/525,277.

Notice of Allowance dated Jun. 25, 2009 in co-pending U.S. Appl. No. 10/525,277.

Non-final Office Action dated Nov. 25, 2009 in co-pending U.S. Appl. No. 10/525,277.

Non-final Office Action dated May 21, 2010 in co-pending U.S. Appl. No. 10/525,277.

Final Office Action dated Nov. 9, 2010 in co-pending U.S. Appl. No. 10/525,277.

Notice of Allowance dated Jan. 20, 2011 in co-pending U.S. Appl. No. 10/525,277.

Non-final Office Action dated May 23, 2012 in co-pending U.S. Appl. No. 13/087,770.

Fujimoto, Y., et al., Angiotension II Type 1 Receptor in Human Pancreatic Cancer ANd Growth Inhibition by Angiotension II Type 1 Receptor Antagonist, FEBS Letters, 2001;495:197-200.

Tamarat, R., et al., Angiotensin II angiogenic effect in vivo involves vascular endothelial growth factor- and inflammation-related pathways, Lab Invest. Jun. 2002:82(6):747-56.

Humphries, M. J., et al., Conjugation of Synthetic Peptides to Carrier Proteins for Cell Adhesion Studies, Journal of Tissue Culture Methods, 1994;16:239-242.

Ezzell, Cancer "Vaccines": An Idea Whose Time Has Come?, J. NIH Res, 1995;7:46-49.

Boon, T., Toward a Genetic Analysis of Tumor Rejection Antigens, Advances in Cancer Research, 1992;58:177-210.

Degruijl, T. D., et al., Cancer vaccine strategies get bigger and better, Nature Medicine, Oct. 1999;5 (10):1124-1125.

Ngo, et al., In The Protein Folding Problem and Tertiary Structure Prediction, 1994;433 and 492-495, Merz, et al., (ed.), Birkhauser, Boston, MA.

Burgess, W. H., et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. of Cell Biology, Nov. 1990;111:2129-2138.

Lazar, E. et al., Transforming Growth Factor Beta: Mutation of Aspartic Acid 47 and Leucine 48 Results in Different Biological Activities, Molecular and Cellular Biology, Mar. 1988;8(3):1247-1252.

Colman, P. M.., et al., Effects of amino acid sequence changes on antibody-antigen interactions, Research in Immunology, 1994;145(1):33-36.

Ling, S. et al., Matrix-dependent gene expression of egr-1 and PDGF A regulate angiotensin II-induced proliferation in human vascular smooth muscle cells, Hypertension. Nov. 1999;34(5):1141-6.

Marsigliate, et al., AT1 angiotensin II receptor subtype in the human larynx and squamous laryngeal carcinoma, Cancer, 1996;110:19-27.

International Search Report dated Apr. 21, 2004 for International Application No. PCT/GB03/03758.

Non-Final Office Action for co-pending U.S. Appl. No. 10/525,277 dated Dec. 4, 2008.

Notice of Allowance for co-pending U.S. Appl. No. 10/525,277 dated Jun. 25, 2009.

Non-Final Office Action for co-pending U.S. Appl. No. 10/525,277 dated Nov. 25, 2009.

Non-Final Office Action for co-pending U.S. Appl. No. 10/525,277 dated May 21, 2010.

Final Office Action for co-pending U.S. Appl. No. 10/525,277 dated Nov. 9, 2010.

Notice of Allowance dated Oct. 24, 2012 issued in co-pending U.S. Appl. No. 13/087,770.

Fukuda, N., et al., MolBi-4 Regulation of growth capability and TGF-_receptor expression due to angiotensin II Type 1 and Type II receptors in vascular smooth muscle cells, Japanese Journal of Clinical Physiology, 2000;30, supplement:115.

Ishida, J., et al., [Angiotensin II and apoptosis], Nihon Rinsho. May 1999;57(5):1117-23.

Final Office Action dated Sep. 2012 in co-pending U.S. Appl. No. 13/087,770.

* cited by examiner

* significant vs control
significant vs 5 nM scFv

```
CLUSTAL W (1.82) multiple sequence alignment

R6313clone12D    YAAQPAMAQVKLQQSGPELEKPGASVKISCKASGYSFTGYTMNWVKQSNGKSLEWIGNID
R6313clone11B    YAAQPAMAQVQLQESGPELEKPGASVKISCKASGYSFTGYNMSWVKQSNGKSLEWIGNID
                 *********::**:.***********************.********************

R6313clone12D    PYYGGTTYNQKFKGKATLTVDKSSSTAYMQLKSLTSEDSAVYYCAREVDYWGQGTTVTVS
R6313clone11B    PYYGGTTYNQKFKGKATLTVDKSSSTAYMQLKSLTSEDSAVYYCAREVDYWGQGTTVTVS
                 ************************************************************

R6313clone12D    SGGGGSGGGGSGGGGSDIELTQSPASLAVSLGQRATISYRASKSVSTSGYSYMHWNQQKP
R6313clone11B    SGGGGSGGGGSGGGGSDIELTQSPASLAVSLGQRATISYRASKSVSTSGYSYMHWNQQKP
                 ************************************************************

R6313clone12D    GQPPRLLIYLIVSNLESGVPARFSGSGSGTDFTLNIHPVEEEDAATTYCQHIRELTRSEGT
R6313clone11B    GQPPRLLIYLIVSNLESGVPARFSGSGSGTDFTLNIHPVEEEDAATTYCQHIRELTRSEGT
                 ************************************************************

R6313clone12D    KLEIKRAAAAGAPVPY
R6313clone11B    KLEIKRAAAAGAPVPY
                 ****************
```

FIG. 10

```
                    ****                              VHCDR1              VHCDR2
                                                *
12D   1  YAAQPAMAQVQLQQSGPELEKPGASVKISCKASGYSFTGYNMNWVKQSNGKSLEWIGNID
11B   1  YAAQPAMAQVQLQQSGPELEKPGASVKISCKASGYSFTGYNMSWVKQSNGKSLEWIGNID
10D   1  YAAQPAMAQVQLQQSGPELEKPGASVKISCKASGYSFTGYNMSWVKQSNGKSLEWIGNID
10E   1  YAAQPAMAQVQLQQSGPELEKPGASVKISCKASGYSFTGYNMSWVKQSNGKSLEWIGNID
4F    1  YAAQPAMAQVQLQQSGPELEKPGASVKISCKASGYSFTGYNMSWVKQSNGKSLEWIGNID
6C    1  YAAQPAMAQVQLQQSGPELEKPGASVKISCKASGYSFTGYNMSWVKQSNGKSLEWIGNID
6E    1  YAAQPAMAQVQLQSSGPELEKPGASVKISCKASGYSFTGYNMSWVKQSNGKSLEWIGNID
7F    1  YAAQPAMAQVQLQQSGPELEKPGASVKISCKASGYSFTGYNMSWVKQSNGKSLEWIGNID
8B    1  YAAQPAMAQVQLQQSGPELEKPGASVKISCKASGYSFTGYNMSWVKQSNGKSLEWIGNID
8C    1  YAAQPAMAQVQLQQSGPELEKPGASVKISCKASGYSFTGYNMSWVKQSNGKSLEWIGNID
8D    1  YAAQPAMAQVQLQQSGPELEKPGASVKISCKASGYSFTGYNMSWVKQSNGKSLEWIGNID
8E    1  YAAQPAMAQVRLQQSGPELEKPGASVKISCKASGYSFTGYNMSWVKQSNGKSLEWIGNID
```

```
           VHCDR2                  *                    VHCDR3         *
12D   61 PYYGGTTYNQKFKGKATLTVDKSSSTAYMQLKSLTSEDSAVYYCAREVDYWGQGTTVTVS
11B   61 PYYGGTTYNQKFKGKATLTVDKSSSTAYMQLKSLTSEDSAVYYCAREVDYWGQGTTVTVS
10D   61 PYYGGTTYNQKFKGKATLTVDKSSSTAYMQLKSLTSEDSAVYYCAREVDYWGQGTTVTVS
10E   61 PYYGGTTYNQKFKGKATLTVDKSSSTAYMQLKSLTSEDSAVYYCAREVDYWGQGTTVTVS
4F    61 PYYGGTTYNQKFKGKATLTVDKSSSTAYMQLKSLTSEDSAVYYCAREVDYWGQGTTVTVS
6C    61 PYYGGTTYNQKFKGKATLTVDKSSSTAYMQLKSLTSEDSAVYYCAREVDYWGQGTTVTVS
6E    61 PYYGGTTYNQKFKGKATLTVDKSSSTAYMQLKSLTSEDSAVYYCAREVDYWGQGTTVTVS
7F    61 PYYGGTTYNQKFKGKATLTVDESSSTAYMQLKSLTSEDSAVYYCAREVDYWGQGTTVTVS
8B    61 PYYGGTTYNQKFKGKATLTVDKSSSTAYMQLKSLTSEDSAVYYCAREVDYWGQGTTVTVS
8C    61 PYYGGTTYNQKFKGKATLTVDKSSSTAYMQLKSLTSEDSAVYYCAREVDYWGQGTTVTVS
8D    61 PYYGGTTYNQKFKGKATLTVDKSSSTAYMQLKSLTSEDSAVYYCAREVDYWGQGTTVTVS
8E    61 PYYGGTTYNQKFKGKATLTVDKSSSTAYMQLKSLTSEDSAVYYCAREVDYWGRGTTVTVS
```

```
              LINKER              *                       VLCDR1
12D  121 SGGGGSGGGGSGGGGSDIELTQSPASLAVSLGQRATISYRASKSVSTSGYSYMHWNQQKP
11B  121 SGGGGSGGGGSGGGGSDIELTQSPASLAVSLGQRATISYRASKSVSTSGYSYMHWNQQKP
10D  121 SGGGGSGGGGSGGGGSDIVLTQSPASLAVSLGQRATISYRASKSISTSGYSYMHWNQQKP
10E  121 SGGGGSGGGGSGGGGSDIELTQSPASLAVSLGQRATISYRASKSVSTSGYSYMHWNQQKP
4F   121 SGGGGSGGGGSGGGGSDIELTQSPASLAVSLGQRATISYRASKSVSTSGYSYMHWNQQKP
6C   121 SGGGGSGGGGSGGGGSDIELTQSPASLAVSLGQRATISYRASKSVSTSGYSYMHWNQQKP
6E   121 SGGGGSGGGGSGGGGSDIELTQSPASLAVSLGQRATISYRASKSVSTSGYSYMHWNQQKP
7F   121 SGGGGSGGGGSGGGGSDIELTQSPASLAVSLGQRATISYRASKSVSTSGYSYMHWNQQKP
8B   121 SGGGGSGGGGSGGGGSDIELTQSPASLAVSLGQRATISYRASKSVSTSGYSYMHWNQQKP
8C   121 SGGGGSGGGGSGGGGSDIVLTQSPASLAVSLGQRATISYRASKSVSTSGYSYMHWNQQKP
8D   121 SGGGGSGGGGSGGGGSDIELTQSPASLAVSLGQRATISYRASKSVSTSGYSYMHWNQQKP
8E   121 SGGGGSGGGGSGGGGSDIELTQSPASLAVSLGQRATISYRASKSVSTSGYSYMHWNQQKP
```

SYNTHETIC SCFV ANALOGUE TO THE 6313/G2 (ANTI ANGIOTENSIN II TYPE 1 RECEPTOR) MONOCLONAL ANTIBODY VARIABLE REGIONS

CROSS-REFERENCE TO RELATED APPLICATIONS

This application is the U.S. National Stage filing of International Application Serial No. PCT/GB2009/000443 filed Feb. 18, 2009, which claims priority to Great Britain Application No. 0802931.6 filed Feb. 18, 2008, each of which is incorporated herein by reference in its entirety.

The present invention relates to a synthetic scFv analogue (R6313/G2) of the 6313/G2 anti angiotensin II type 1 receptor monoclonal antibody variable domains.

Angiotensin-II plays a central role in mammalian electrolyte homeostasis and blood pressure control (Peach *Physiol. Rev* 57 313-370 (1977); Vinson et al *"The Adrenal Cortex"*, Prentice Hall, Englefield Heights (1992)). Two main types of angiotensin-II receptors, designated types 1 and 2 (AT1 and AT2), have been recognised, but the majority of the well known actions of angiotensin-II occur via the AT1 subtype (Herblin et al *Am. J. Hypertens.* 4 299S-302S (1991); Ouali et al *J. Steroid. Biochem. Mol. Biol.* 43 271-280 (1992)).

A monoclonal antibody 6313/G2 to the AT1 receptor subtype (Barker et al *J. Mol. Endocrinol.* 11 241-245 (1993)) has been used to study the distribution of the receptor (Vinson et al *Mol. Med. Today* 1 35-38 (1995)). The monoclonal antibody has been suggested for use as a therapeutic agent to control vaso-constriction, for example in the treatment of hypertension or other smooth muscle cell (e.g. uterine) contraction.

The antibody has been used as a specific imaging agent in various tissues, for example laryngeal cancer (Marsigliante et al *Cancer Letters* 110 19-27 (1996)), kidney (Harrison-Bernard et al *Am. J. Physiol.* 42 F170-F177 (1997); Cheng et al *Am. J. Physiol.* 43 F10-F17 (1998)), and brain (Yang et al *J. Neuroscience* 17 1660-1669 (1997)). The antibody has been shown to block angiotensin-II induced AT1 receptor internalisation and PKC activation but conversely promotes the calcium response (Kapas et al *Biochem. Biophys. Res. Comm.* 204 1292-1298 (1994); Vinson et al *J. Endocrinol.* 141 R5-R9 (1994)). The presence of AT1 and AT2 receptors in breast tumours has been reported with local production of angiotensin (Inwang et al *Brit. J. Cancer* 75 1279-1283 (1997); Tahmasebi et al *Eur. J. Cancer* 34 1777-1782 (1998)).

Monoclonal antibody 6313/G2 is secreted by a hybridoma cell line deposited on 21 Jul. 1993 with the European Collection of Animal Cell Cultures (ECACC), Porton Down, United Kingdom, under the Budapest Treaty, and designated by the accession no. 93072117. The deposit was made by Dr Gavin P Vinson and Dr Stewart Barker, Department of Biochemistry, Queen Mary & Westfield College, Mile End Road, London E1 4NS. The depositor has authorised the applicant to refer to the deposited material in the application and has given his unreserved and irrevocable consent to the deposited material being made available to the public in accordance with Rule 28(1)(d) of the European Patent Convention.

The hybridoma cell line produces an antibody that specifically binds to amino acid residues 8 to 17 of the rat vascular smooth muscle AT1 receptor, which sequence is also found in the AT1 receptor of human and bovine cells. The epitope sequence is as follows: EDGIKRIQDD (SEQ ID NO: 1)

Or, alternately expressed as, (SEQ ID NO: 1)
NH$_2$-Glu-Asp-Gly-Ile-Lys-Arg-Ile-Gln-Asp-Asp-COOH Monoclonal antibodies to the peptide sequence comprising the N-terminal sequence of the angiotensin-II type-1 receptor have been prepared (Barker et al *Journal of Molecular Endocrinology* 11 241-245 (1993); WO 95/09186). It has been reported that such monoclonal antibodies have additional therapeutic uses in certain medical conditions where such uses were not previously suggested or shown (WO2004/018519). These therapeutic effects are seen in the ability of the monoclonal antibodies to block the harmful actions of angiotensin-II in the medical conditions concerned whilst preserving the beneficial actions of the molecule.

It has now been found that synthetic scFv analogues of monoclonal antibodies specific for the AT1 receptor possess advantageous and unexpected properties which provide for the use of such analogues in the therapy or treatment of diseases. The inventors have produced both murine scFv analogues and humanised variants of the murine scFv analogues.

According to a first aspect of the invention, there is provided a specific binding molecule which specifically binds to a peptide having the amino acid sequence of EDGIKRIQDD (SEQ ID NO:1) and comprises a polypeptide having an immunoglobulin V$_L$ domain linked to an immunoglobulin V$_H$ domain in which the V$_L$ domain comprises Complementarity Determining Regions (CDRs) VLCDR1, VLCDR2 and VLCDR3, and in which the V$_H$ domain comprises Complementarity Determining Regions (CDRs) VHCDR1, VHCDR2, VHCDR3, each having a respective amino acid sequence as follows in which

| | | |
|---|---|---|
| VHCDR1 is GYSFTGYNMN | (SEQ ID NO: 2) |
| VHCDR2 is NIDPYYGGTTYNQKFKG | (SEQ ID NO: 3) |
| VHCDR3 is EVDY | (SEQ ID NO: 4) |
| VLCDR1 is RASKSVSTSTSGYSYMH | (SEQ ID NO: 5) |
| VLCDR2 is LVSNLES | (SEQ ID NO: 6) |
| VLCDR3 is QHIRELTRSEG | (SEQ ID NO: 7) | or an amino acid sequence at least 70% identical thereto.

In one embodiment, the present invention provides a specific binding molecule which specifically binds to a peptide having the amino acid sequence of EDGIKRIQDD (SEQ ID NO:1) and comprises a polypeptide having an immunoglobulin V$_L$ domain linked to an immunoglobulin V$_H$ domain in which the V$_L$ domain comprises Complementarity Determining Regions (CDRs) VLCDR1, VLCDR2 and VLCDR3, and in which the V$_H$ domain comprises Complementarity Determining Regions (CDRs) VHCDR1, VHCDR2, VHCDR3, each having a respective amino acid sequence as follows in which

| | |
|---|---|
| VHCDR1 is GYSFTGYNMN (SEQ ID NO: 2) or GYSFTGYNMS (SEQ ID NO: 8) | |
| VHCDR2 is NIDPYYGGTTYNQKFKG | (SEQ ID NO: 3) |

```
VHCDR3 is EVDY                                    (SEQ ID NO: 4)

VLCDR1 is RASKSVSTSTSGYSYMH                       (SEQ ID NO: 5)

VLCDR2 is LVSNLES                                 (SEQ ID NO: 6)

VLCDR3 is QHIRELTRSEG                             (SEQ ID NO: 7)
``` or an amino acid sequence at least 80% identical thereto.

In another embodiment of the invention the CDRs of the specific binding molecule have amino acid sequences as follows

```
VHCDR1 is GYSFTGYNMN (SEQ ID NO: 2) or GYSFTGYNMS (SEQ ID NO: 8)

VHCDR2 is NIDPYYGGTTYNQKFKG                       (SEQ ID NO: 3)

VHCDR3 is EVDY                                    (SEQ ID NO: 4)

VLCDR1 is RASKSVSTSGYSYMH                         (SEQ ID NO: 5)

VLCDR2 is LVSNLES (SEQ ID NO: 6) or LVSDLED       (SEQ ID NO: 9)

VLCDR3 is QHIRELTRSEG.                            (SEQ ID NO: 7)
```

The CDRs are designated according to a combination of conserved sequence definition (Kabat et al in "Sequences of Proteins of Immunological Interest", Nat'l. Inst. Health, Bethesda, Md. (1987)), and structural definition (Chothia and Lesk *J. Mol. Biol.* 196:901-17 (1987)). These definitions were also subsequently described in Carter et al, *Proc Nat'l Acad Sci USA*. 89:4285-9 (1992).

Using the three letter and one letter codes the amino acids may also be referred to as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and glutamic acid include glutamate, unless the context specifies otherwise.

The present invention also extends to variants of peptide sequences referred to above. An example of a variant of the present invention is a fusion protein comprising a peptide as defined above, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This may be done to alter the properties of a substance of the present invention (e.g. to assist in identification, purification or expression, as explained above in relation to fusion proteins).

Amino acid changes relative to the sequence given above can be made using any suitable technique e.g. by using site-directed mutagenesis or solid state synthesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. 215, 403 (1990).

Preferably, the amino acid sequence of the CDRs of the invention have at least 70% identity, using the default parameters of the BLAST computer program (Atschul et al., J. Mol. Biol. 215, 403-410 (1990) provided by HGMP (Human Genome Mapping Project), at the amino acid level, to the amino acid sequences of the $V_H$ and $V_L$ CDRs described above.

More preferably, the CDR sequence may have at least 75%, 80%, 85%, 90%, 95%, 96%, 97%, 98% or at least 99% identity, at the amino acid level, to the sequences shown above.

In one embodiment of the invention, the specific binding molecule may have one of the following arrangement of CDRs

```
(R6313clone12D and humanised variants HuCY and
var3)
VHCDR1:  GYSFTGYNMN          (SEQ ID NO: 2)

VHCDR2:  NIDPYYGGTTYNQKFKG   (SEQ ID NO: 3)

VHCDR3:  EVDY                (SEQ ID NO: 4)

VLCDR1:  RASKSVSTSGYSYMH     (SEQ ID NO: 5)

VLCDR2:  LVSNLES             (SEQ ID NO: 6)

VLCDR3:  QHIRELTRSEG         (SEQ ID NO: 7)
or (R6313clone11B)
VHCDR1:  GYSFTGYNMS          (SEQ ID NO: 8)

VHCDR2:  NIDPYYGGTTYNQKFKG   (SEQ ID NO: 3)

VHCDR3:  EVDY                (SEQ ID NO: 4)

VLCDR1:  RASKSVSTSGYSYMH     (SEQ ID NO: 5)

VLCDR2:  LVSNLES             (SEQ ID NO: 6)

VLCDR3:  QHIRELTRSEG         (SEQ ID NO: 7)
or
(Humanised variant var4)
VHCDR1:  GYSFTGYNMN          (SEQ ID NO: 2)

VHCDR2:  NIDPYYGGTTYNQKFKG   (SEQ ID NO: 3)

VHCDR3:  EVDY                (SEQ ID NO: 4)

VLCDR1:  RASKSVSTSGYSYMH     (SEQ ID NO: 5)

VLCDR2:  LVSDLED             (SEQ ID NO: 9)

VLCDR3:  QHIRELTRSEG.        (SEQ ID NO: 7)
```

In one embodiment of the invention, the specific binding molecule may comprise a variable heavy chain ($V_H$) and a variable light chain ($V_L$) connected by a peptide linker. The linker may comprise from 1 to 20 amino acids, such as for example 1, 2, 3 or 4 amino acids, 5, 10 or 15 amino acids, or other intermediate numbers in the range 1 to 20 as convenient. The peptide linker may be formed from any generally convenient amino acid residues, such as glycine and/or serine. One example of a suitable linker is $Gly_4Ser$. Multimers of such linkers may be used, such as for example a dimer, a trimer, a tetramer or a pentamer, e.g. $(Gly_4Ser)_2$, $(Gly_4Ser)_3$, $(Gly_4Ser)_4$ or $(Gly_4Ser)_5$. However, in other embodiments of the invention no peptide linker may be present and the $V_L$ domain may be linked to the $V_H$ domain by a peptide bond.

The specific binding molecule may be a single-chain variable analogue (scFv). The specific binding molecule or scFv may be linked to other specific binding molecules (for example other scFvs, Fab antibody fragments, chimeric IgG antibodies (e.g. with human frameworks)) or linked to other scFvs of the invention so as to form a multimer which is a multi-specific binding protein, for example a dimer, a trimer or a tetramer. Bi-specific scFv's are sometimes referred to as diabodies, tri-specific such as triabodies and tetra-specific such as tetrabodies when each scFv in the dimer, trimer or tetramer has a different specificity. Diabodies, triabodies and tetrabodies can also be monospecific, when each scFv in the dimer, trimer or tetramer has the same specificity.

In one embodiment of the invention, the specific binding molecule may be the monoclonal antibody analogue scFv identified as R6313/G2. This scFv is also referred to herein as R6313clone12D or clone 12D and has the sequence shown in FIG. 14. In another embodiment of the invention, the specific binding molecule may be the monoclonal antibody analogue scFv identified as R6313clone11B, also referred to herein as clone 11B, whose sequence is also shown in FIG. 14.

The scFv may be prepared by any suitable technique using standard chemical or molecular biology techniques. In one embodiment of the invention, the monoclonal antibody analogues can be prepared as scFv's from a naïve human antibody phage display library (McCafferty et al., Nature 348, 552-554 (1990); and as described in WO 92/01047).

The monoclonal antibody analogue may be humanised by modifying the amino acid sequence of the scFv. Methods to reduce the immunogenicity of the specific binding molecules of the invention may include CDR grafting on to a suitable antibody framework scaffold or variable surface residues remodelling, e.g. by site-directed mutagenesis or other commonly used molecular biological techniques (Roguska et al *Protein Eng.* 9 895-904 (1996)).

Other methods applicable can include the identification of potential T-cell epitopes within the molecule, and the subsequent removal of these e.g. by site-directed mutagenesis (de-immunisation). Humanisation of the specific binding molecule may be desired where the molecule is to be used as a therapeutic agent. Humanisation of the CDR regions or of the surrounding framework sequence may be carried out as desired.

The present inventors have produced humanised variants of the scFv R6313/G2, as described in the Examples.

In one embodiment of the invention, the specific binding molecule may be any one or more of the humanised scFvs identified as HuCY, var3 and/or var4. The sequences of these humanised scFvs are shown in FIG. 14.

In another aspect of the invention there is provided a pharmaceutical composition comprising a specific binding molecule as described above.

The composition used in accordance with this aspect of the invention may be formulated for use by any convenient route. The medicament will usually be supplied as part of a sterile, pharmaceutical composition which will normally include a pharmaceutically acceptable carrier. The compositions of the invention may be employed in combination with a pharmaceutically acceptable carrier or carriers or a pharmaceutically acceptable adjuvant and/or diluent. Such carriers may include, but are not limited to, saline, buffered saline, dextrose, liposomes, water, glycerol, polyethylene glycol, ethanol and combinations thereof. This pharmaceutical composition may be in any suitable form (depending upon the desired method of administering it to a patient).

It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions)

Suitable excipients for tablets or hard gelatine capsules include lactose, maize starch or derivatives thereof, stearic acid or salts thereof.

Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists that may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

In some embodiments, the formulation of the active drug concentrate may comprise a pharmaceutically acceptable tonicity agent, a buffering agent, and a pharmaceutically acceptable surfactant.

Alternatively, the formulation may comprise the active ingredient plus sodium phosphate, monobasic, sodium phosphate dibasic, sodium chloride, polysorbate 80 or polysorbate 20 (surfactant to minimise risk of agitation-induced aggregation) and water (USP/Ph. Eur), optionally with a pH adjusted to about 6.0 to 7.0, e.g. around 6.5

The active drug concentrate may or may not be lyophilised.

Other formulations may comprise sodium acetate trihydrate as a buffering agent, sodium chloride as a tonicity modifier, acetic acid for pH adjustment, and water for injection.

The active drug concentrate may also be diluted in 0.9% sodium chloride prior to administration.

Dosages of the substance of the present invention can vary between wide limits, depending upon the disease or disorder to be treated, the age and condition of the individual to be treated, etc. and a physician will ultimately determine appropriate dosages to be used.

This dosage may be repeated as often as appropriate. If side effects develop the amount and/or frequency of the dosage can be reduced, in accordance with normal clinical practice.

For administration to mammals, and particularly humans, it is expected that the daily dosage of the active agent will be from 1 µg/kg to 10 mg/kg body weight, typically around 10 µg/kg to 1 mg/kg body weight. The physician in any event will determine the actual dosage which will be most suitable for an individual which will be dependant on factors including the age, weight, sex and response of the individual. The above dosages are exemplary of the average case. There can, of course, be instances where higher or lower dosages are merited, and such are within the scope of this invention.

The specific binding molecules as described above can be used in medicine, for example in the treatment of cancer. Without wishing to be bound by theory, it is believed that cancers which contain the angiotensin type-1 receptor (AT1R) may be particularly susceptible to therapy using the specific binding molecules of the invention. Such cancers are numerous and include breast cancer, prostate cancer, ovarian cancer, uterine cancer, colorectal cancer, pancreatic cancer, pituitary gland cancer, choriocarcinoma, Hodgkins disease, skin cancer, kidney cancer, adrenal tumours, liver cancer, lung cancer, leukaemia and neuroblastoma cells.

This aspect of the invention therefore also includes a method for the treatment of cancer in a subject, comprising administering to the subject a specific binding molecule as described above. The invention therefore also extends to the use of a specific binding molecule as described above in the manufacture of a medicament for use in the treatment of cancer. The method of treatment may of a human or an animal subject and the invention extends equally to uses in both human and/or veterinary medicine.

In a further aspect of the invention, there is provided a combined preparation of a specific binding molecule as described above and angiotensin-II for the separate, simultaneous or subsequent administration for the treatment of cancer in a subject. The cancer may be as described above.

The invention also provides a composition comprising a specific binding molecule of the invention as defined above and angiotensin-II. Such compositions may be formulated as a pharmaceutical composition comprising a pharmaceutically acceptable adjuvant and/or diluent.

Alternatively, the invention also provides a kit of parts comprising a specific binding molecule of the invention and angiotensin II each formulated for pharmaceutical administration including, but not limited to, as tablets for oral administration, inhalers for lung administration and injectable solutions for intravenous administration.

Embodiments of the invention relating to the use of angiotensin II may comprises any generally convenient form of angiotensin suitable for use in human or veterinary medicine. Suitably, the angiotensin II may be supplied in the form of a freeze dried product in which the residue is derived from a solution that contained Angiotensin II, trehalose, human serum albumin and acetic acid. One source of pharmaceutical grade angiotensin II is NIBSC, South Mimms, UK which supplies Angiotensin II in the form of an ampoule containing freeze-dried residue prepared from 0.5 ml of a solution a solution comprising 2.5 µg Angiotensin II (Ileu5), 3 mg trehalose, 1 mg human serum albumin, $2 \times 10^{-3}$ mol/l acetic acid.

Synthetic analogues of the variable regions of the 6313/G2 monoclonal antibody, such as the scFv referred to as R6313/G2, have unique and advantageous properties, especially when compared with the original hybridoma antibody. For example:

1. In intact nu/nu mice bearing cancer cells in hollow fibers, R6313/G2 significantly inhibited cancer cell growth. This is surprising because at concentrations of 13 nmol/kg 2× per day, it had no effect on body weight, circulating aldosterone concentrations, or animal activity, i.e. other angiotensin related functions were unaffected. (Note: the original hybridoma antibody increased aldosterone secretion in vitro).
2. R6313/G2 alone inhibits T-47D cell invasion through reconstituted basement membrane matrix proteins (ECM) derived from the Engelbroth-Holm-Swam (EHS) mouse tumour at concentrations of 50 and 250 nmol/L (see FIG. 9(b)). The purified monoclonal antibody (at 100 nmol/L) has no significant inhibitory effect. Furthermore, in the presence of angiotensin II at 100 nmolL (in FIG. 9(b)) the effect of the R6313/G2 becomes significantly more pronounced at the highest concentration of R6313/G2 (250 nmol/L)—up to 25% inhibition of cell invasion over the 24 hour assay period.
3. In the presence of up to 100 nmol angiotensin II per L R6313/G2, significantly inhibits breast cancer cell proliferation. This is surprising because the presence of angiotensin II is required, and R6313/G2 has no effect in the absence of angiotensin II
4. In intact rats in vivo, R6313/G2 significantly inhibits the stress-induced increases in blood pressure. This is surprising because it does not reduce and may even increase resting blood pressure.
5. In the presence, but not the absence, of up to 100 nmol angiotensin II per L, R6313/G2 enhances caspase-driven apoptosis in breast cancer cells. The omission of angiotensin blocks its effects. Hence the presence of angiotensin II is surprisingly required for the activity of the R6313/G2
6. Surprisingly R6313/G2 was greatly more effective in vivo than in vitro. Thus a dose of 25 nmol/Kg in vivo gave an anti-cancer cell effect equivalent to that achieved by 3.3 micromol/L in vitro.
7. In intact nu/nu mice bearing xenograft cancer cell tumours, R6313/G2 significantly inhibited cancer cell growth, at 13 nmol/kg, again without other effects.
8. As can be seen from FIG. 12, there was increased binding to peptide antigen in resurfaced (humanised) scFv versus murine scFv. This therefore presents an advantage in terms of both potential cost per treatment and also gives benefit from having less potential to elicit an immune response in humans. Furthermore, the humanised variant var4 showed the most significantly increased binding compared to the parent murine scFv. This was surprising since the one of the CDRs (VLCDR2) of this variant was modified with respect to the parent murine scFv.

Preferred features for the second and subsequent aspects of the invention are as for the first aspect mutatis mutandis.

In one embodiment, the present invention provides a specific binding molecule which comprises a polypeptide having a sequence shown in FIG. 14.

The present invention will now be further described by way of example with reference to the following Examples which are present for the purposes of illustration only. In the Examples, reference is made to a number of figures in which:

FIG. 1 shows immunoblotting for the angiotensin II receptor subtypes. AT1 receptor (A) and AT2 receptor (B) content was analysed in lysates of three breast cancer cell lines (Lane B, T47D; Lane C, MDA-MB-231; Lane D, MCF-7), and smooth muscle cells (Lane A). Only lysates from the three breast cancer cell lines (Lanes B-D) contained the AT2 receptor, though MDA-MB-231 cells contained relatively little: there was no detectable AT2 receptor in RASMC (Lane A).

FIG. 2 shows (A) dose dependent inhibition of cell survival by R6313/G2 in the presence of 100 nmol angiotensin II per L which was determined by XTT assay after 48 hours. Threshold values (*) for the three cell lines ($P<0.05$ or better) were 0.05 µM for MCF-7 and MDA-MB-231 cells, and 1.25 µM for T47D cells; IC50 values were: 2.8 µmol/L, 1.53 nmol/L and 30 nmol/L for T47D, MDA-MB-231 and MCF-7 cells respectively. (B) Losartan alone produced a 43% inhibition of T47D cells at 25 µmol/L, other cell types were unaffected at all concentrations used. Results are means of eight samples ±S.D.

FIG. 3 shows (A and B) the effect of R6313/G2 on caspase-3/7 activity in T47D cells in the presence and absence of 100 nmol/L angiotensin II after 12 hours and 48 hours. After 12 hours, angiotensin II inhibited caspase-3/7 activity compared with untreated control values and this inhibition was blocked by R6313/G2. This blocking action of R6313/G2 was less marked at the higher doses used, but after 48 hours R6313/G2 alone gave a dose-dependent increase of caspase-3/7 activity. (C) in MCF7 cells, R6313/G2 alone reduced caspase-3/7 activity, but in the presence of angiotensin II it dose dependently increased caspase-3/7 activity. Data are means of eight samples ±S.D. * $P<0.05$, ** $P<0.01$.

FIG. 4 shows (A) In the in vitro hollow fiber assay, R6313/G2 dose dependently inhibited survival of all three breast cell lines (T47D, MCF-7 and MDA-MB-231) in the presence of angiotensin II after 48 h. (B) In the in vivo hollow fiber assay at the s.c. site, R6313/G2 dose dependently inhibited cell survival only in MCF-7 cells, though MDA MB 231 cells were inhibited at the highest dose. (C) In the in vivo hollow fiber assay at the i.p. site, R6313/G2 inhibited MCF7 cell survival in animals treated with 0.07 and 0.7 mg/kg (2.5 and 25 nmol/kg) twice per day, and in T47D and MBA MB 231 cells at 0.7 mg/kg (25 nmol/kg) twice per day. Values are expressed as means±S.D. *P<0.05, **P<0.001. (D) Body weights of the experimental animals showed no changes during the period of treatment.

FIG. 5 shows in vivo R6313/G2 treatment in the animals with MCF7 cell xenograft implants gave no weight loss at doses of 0.4 mg/kg (13 nmol/kg; -■-) and 0.8 mg/kg (27 nmol/kg; -▲-); twice per day, and there was no mortality during the treatment period, but in the 0.8 mg/kg group, four died by day 8. Body weight was significantly reduced in animals receiving 1.36 mg/kg (45.3 nmol/kg; -●-*P<0.05) and all died by day 8. Data are means±S.E.M., n=8, except where indicated otherwise (n numbers in brackets). Control (-♦-).

FIG. 6 shows in vivo actions of R6313/G2 on MCF-7 cell xenografts. (A) MCF-7 tumour volumes, means±S.E.M. (B) Same data as for A, treated values expressed as percentages of the mean control values. *P<0.05, **P<0.001.

FIG. 7 shows sample MCF7 cell xenografts in control (upper) and (lower) after treatment for 7 days with 0.4 mg/kg R6313/G2 twice per day for 7 days, as for FIG. 6.

FIG. 8 shows blood pressures of rats treated with R6313/G2 (scFv, 0.4 mg/kg per day for 3 days) compared with controls (Con) receiving PBS alone. *P<0.05, comparison of Con and ScFv diastolic pressures.

FIG. 9 shows a comparison between the purified monoclonal antibody from hybridoma supernatant (Mab; FIG. 9a) and the scFv, R6313/G2 clone12D (scFv; FIG. 9b), in a cellular invasion assay using T-47D breast cancer cells. In this assay invading cells will have broken through an established model of extracellular matrix. FIG. 9b shows that scFv alone significantly inhibits T-47D cell invasion through reconstituted basement membrane matrix proteins (ECM) derived from the Engelbreth-Holm-Swam (EHS) mouse tumour at concentrations of 50 and 250 nmol/L (b). The purified monoclonal antibody (at 100 nM) has no significant inhibitory effect. Furthermore, in the presence of angiotensin II (Ang II) at 100 nmol/L (in b), the scFv effect becomes significantly more pronounced at the highest concentration of scFv (250 nM).

FIG. 10 shows the alignment of the full sequences of clones 12D (SEQ ID NO:15) and 11B (SEQ ID NO:16). The effective amino acid sequence for the scFv variants begins at amino acid 9, and ends 9 residues from the end, of the sequence presented in this figure. The additional amino acids at each end include part of the pCANTAB 5E vector leader sequence (N-terminal to the scFv sequence), and peptide sequence including part of the E-tag expression peptide (C-terminal to the scFv sequence) that was expressed using the pCANTAB 5E and used in affinity purification of the scFv. In particular, the effective amino acid sequence begins after an MA signal peptidase cleavage site that is part of the periplasmic targeting leader sequence and ends before a triple alanine bridging sequence and the GAPVPY E-tag sequence.

FIG. 11 shows the alignment of the full sequences of clones 12D, 11B, 10D (SEQ ID NO:17), 10E (SEQ ID NO:18), 4F (SEQ ID NO:19), 6C (SEQ ID NO:20), 6E (SEQ ID NO:21), 7F (SEQ ID NO:22), 8B (SEQ ID NO:23), 8C (SEQ ID NO:24), 8D (SEQ ID NO:25) and 8E (SEQ ID NO:26).

FIG. 12 panels a-b represent four separate ELISA comparisons carried out in triplicate. This shows the amount of binding of five different scFv variants to peptide antigen (from AT1-receptor N-terminal region). Data shown as mean±S.E.M. of the absorbance values at 450 nm per mg protein/well after background subtraction.

FIG. 14 shows the alignment of the sequences of clones 12D, 11B and the humanised variants HuCY (SEQ ID NO:27), variant 3 (SEQ ID NO:28) and variant 4 (SEQ ID NO:29).

Figure 15A:
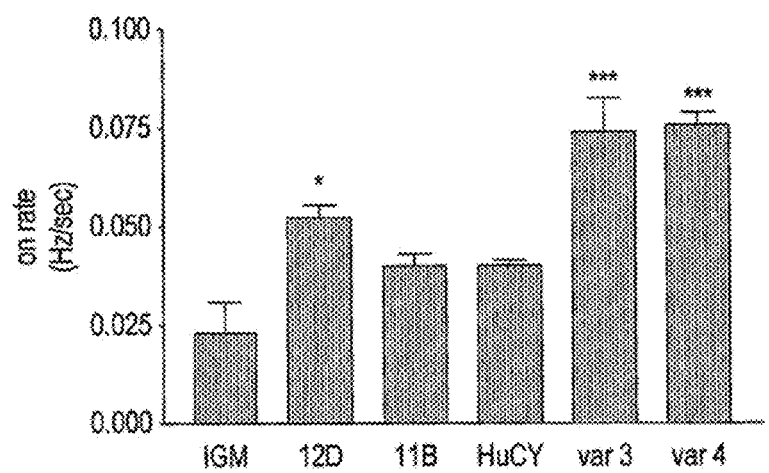
Figure 15B:
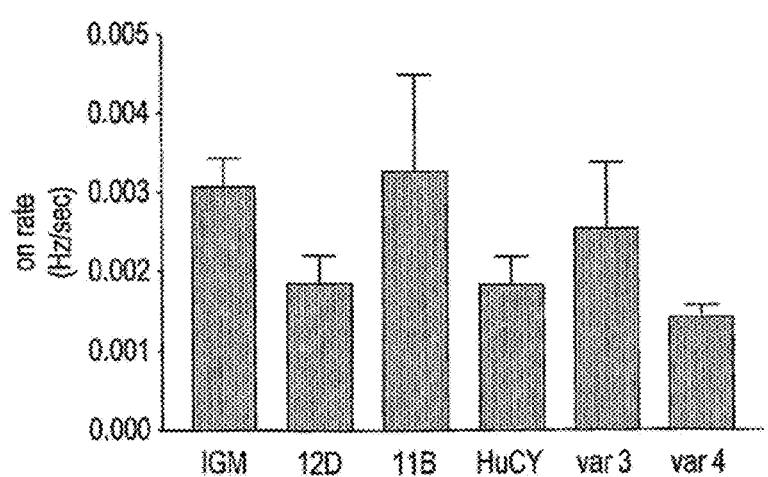

FIG. 15 Panel a) shows a comparison of change in resonance frequency, apparent on-rate in Hz/second, between the IgM and the scFv variants. These data were obtained using an Attana 100 QCM Biosensor and are expressed as mean±S.E.M. of the resonance frequency of a streptavidin-coated QCM chip with biotinylated peptide antigen as binding target. ScFvs 12D, var3 and var4 showed significantly greater changes in resonance frequency over the 100 second injection period. Panel b) compares the apparent off-rates of the various antibody proteins determined similarly. No significant differences in these terminal off-rates were observed under these experimental conditions.

EXAMPLE 1

Preparation of scFv

The 6313/G2 mouse monoclonal antibody hybridoma was grown as previously described (Barker et at *J. Mol. Endocrinol.* 11 241-245 (1993)). A pool of cDNA derived from mRNA was used to obtain heavy and light chains by PCR. A linker fragment encoding $(Gly_4Ser)_3$ was used to assemble the scFv library of inserts and a phage display library was created by directionally cloning these inserts into the pCANTAB 5 E phagemid vector (Amersham Pharmacia, High Wycombe, UK). An E-tag for the expressed sequence GAPVPYPDPLEPR (SEQ ID NO: 11) was included in this vector and used in subsequent panning and purification steps. The phagemid library was then used to transform TG1 *E. coli*, and phagemid rescue was carried out using the M13K07 helper phage followed by several rounds of panning Positive expressing clones were identified by ELISA using 96 well plates coated with the original antigenic peptide (EDG-IKRIQDD; SEQ ID NO:1) and an anti-E-tag antibody (Amersham Pharmacia) detected using an HRP-linked secondary antibody. One particular clone was taken forward for expression and purification and functional assessment on the basis of giving the highest signal in the antigen ELISA.

The 6313/G2 scFv (R6313/G2, clone 12D) was purified using HiTrap E-tag columns (Amersham Pharmacia) followed by purification using a Protein L column (BD Clontech, Cowley, Oxford, UK) which binds immunoglobulins, including scFv. For in vitro and in vivo experiments it was necessary to carry out medium scale purification followed by overnight dialysis against PBS and concentration using 30 kDa cut-off concentrators (Millipore, Watford, UK). The final antibody stock was routinely reconstituted on PBS at a concentration of 10 mg/ml.

Monoclonal antibody used for comparison in invasion assay was purified using immobilised mannan binding protein column (Perbio Science UK Ltd) followed by concentration using 100 kDa molecular weight cut-off filters.

Preliminary studies seem to show highest activity is associated with clones R6313clone12D (also described as R6313/G2) and R6313clone11B, in which the CDRs are as follows:

```
R6313clone12D
VHCDR1:  GYSFTGYNMN           (SEQ ID NO: 2)

VHCDR2:  NIDPYYGGTTYNQKFKG    (SEQ ID NO: 3)

VHCDR3:  EVDY                 (SEQ ID NO: 4)

VLCDR1:  RASKSVSTSGYSYMH      (SEQ ID NO: 5)

VLCDR2:  LVSNLES              (SEQ ID NO: 6)

VLCDR3:  QHIRELTRSEG          (SEQ ID NO: 7)
or
R6313clone11B
VHCDR1:  GYSFTGYNMS           (SEQ ID NO: 8)

VHCDR2:  NIDPYYGGTTYNQKFKG    (SEQ ID NO: 3)

VHCDR3:  EVDY                 (SEQ ID NO: 4)

VLCDR1:  RASKSVSTSGYSYMH      (SEQ ID NO: 5)

VLCDR2:  LVSNLES              (SEQ ID NO: 6)

VLCDR3:  QHIRELTRSEG          (SEQ ID NO: 7)
```

Figure 1A:
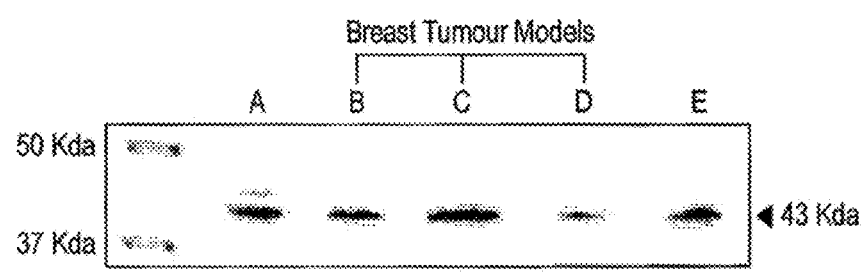
Figure 1B:
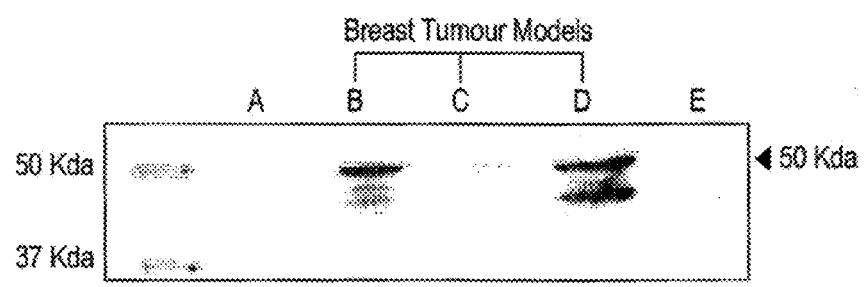
Figure 2A:
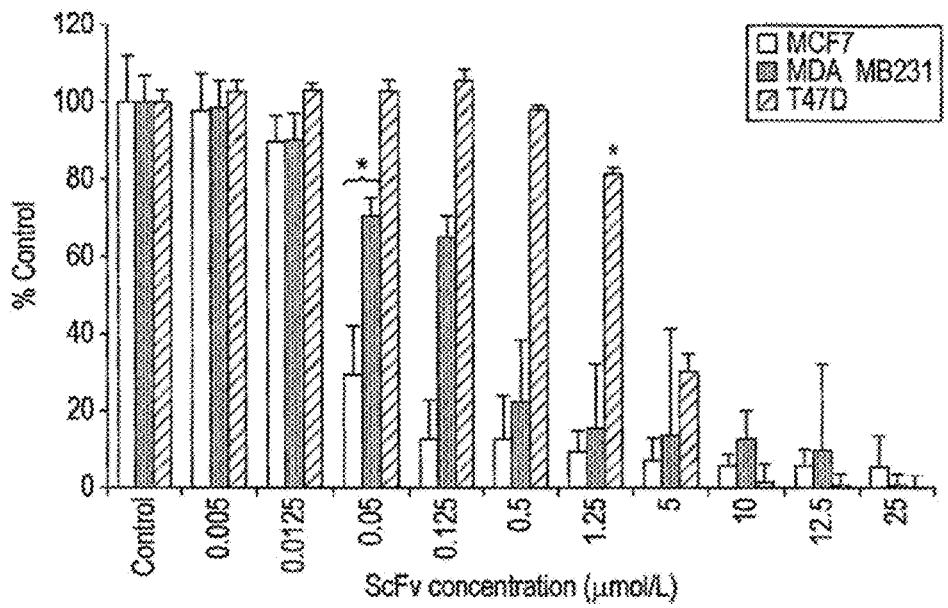
Figure 2B:
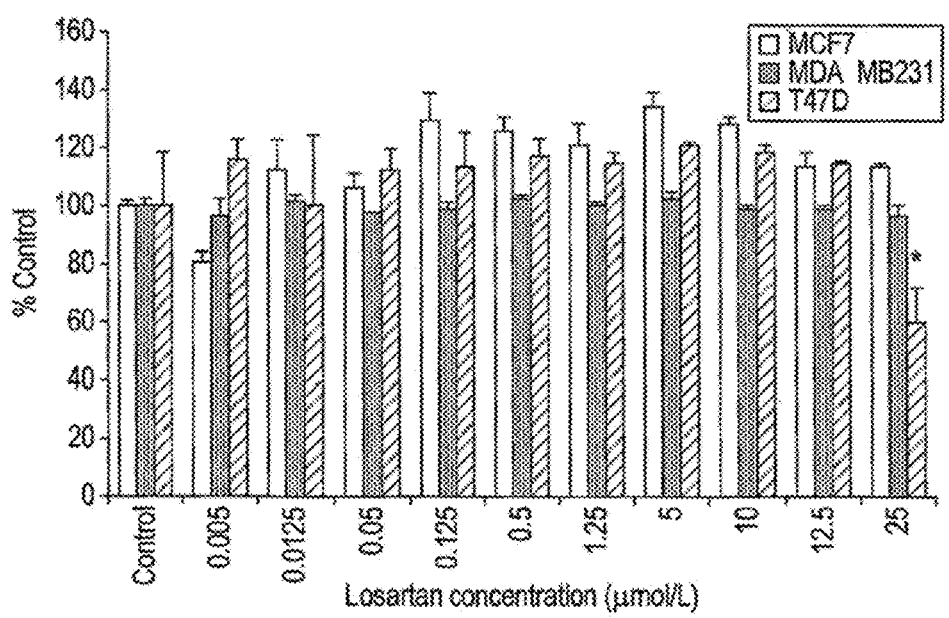
Figure 3A:
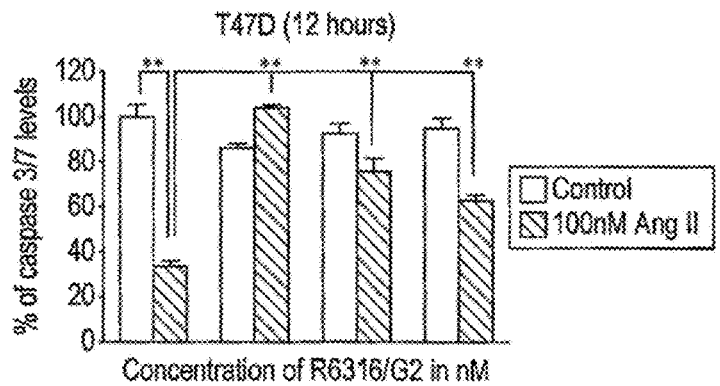
Figure 3B:
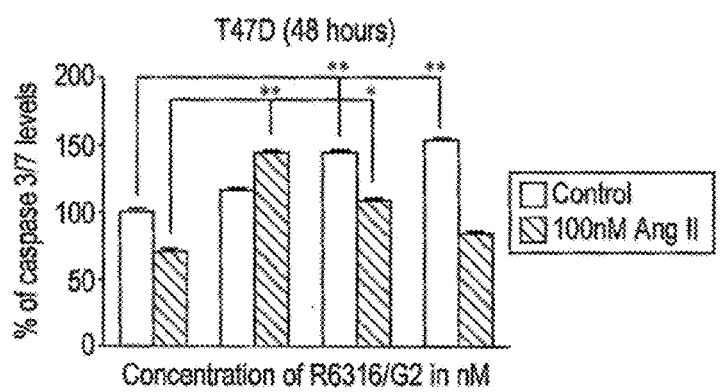
Figure 3C:
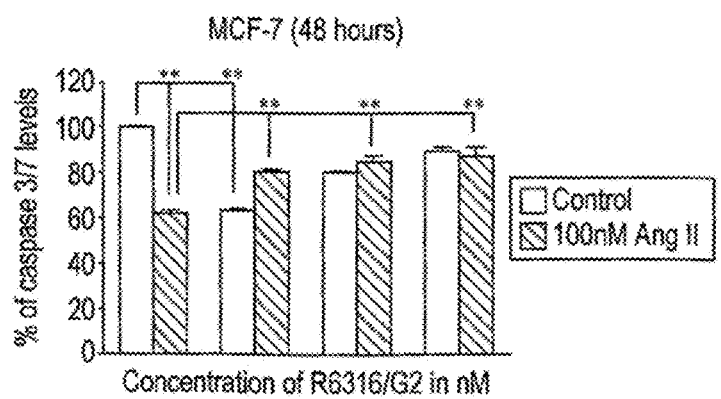
Figure 4A:
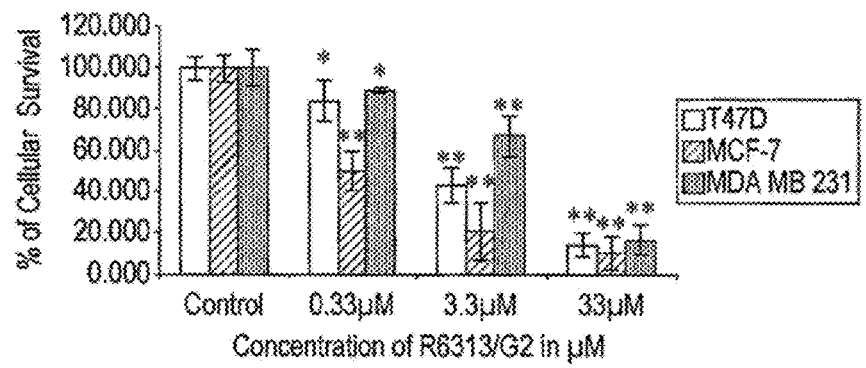
Figure 4B:
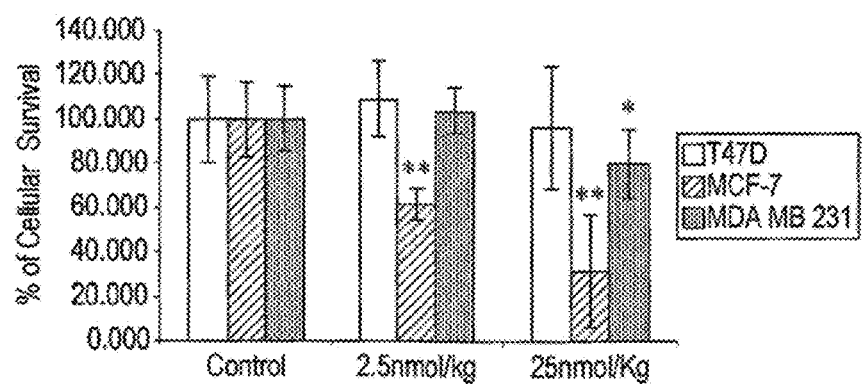
Figure 4C:
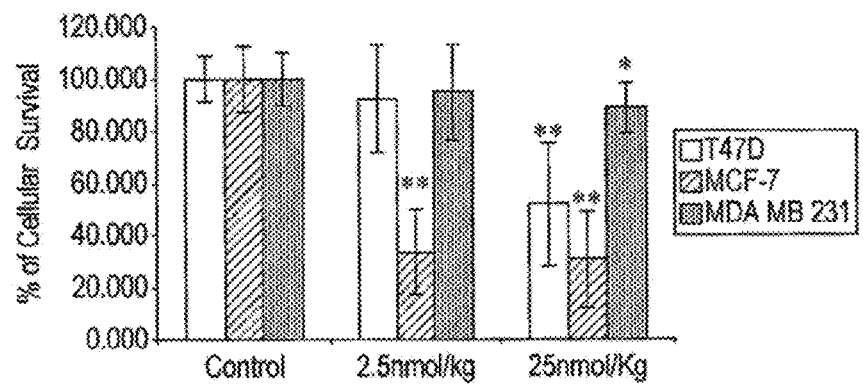
Figure 4D:
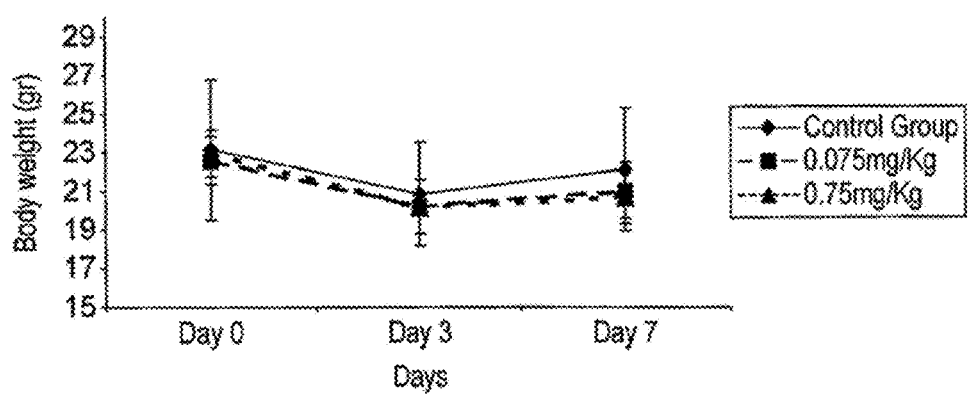
Figure 5:
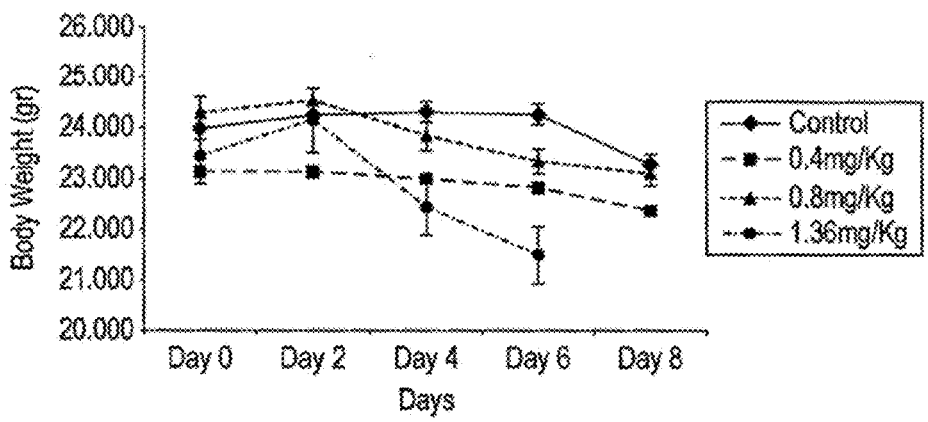
Figure 6A:
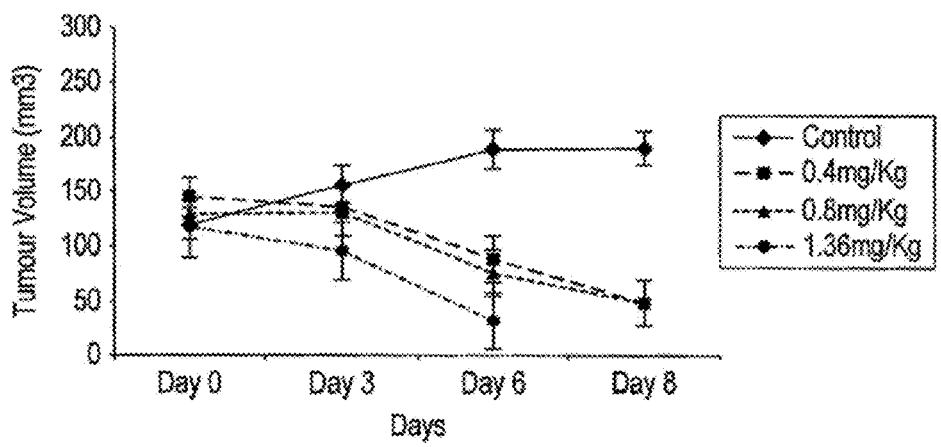
Figure 6B:
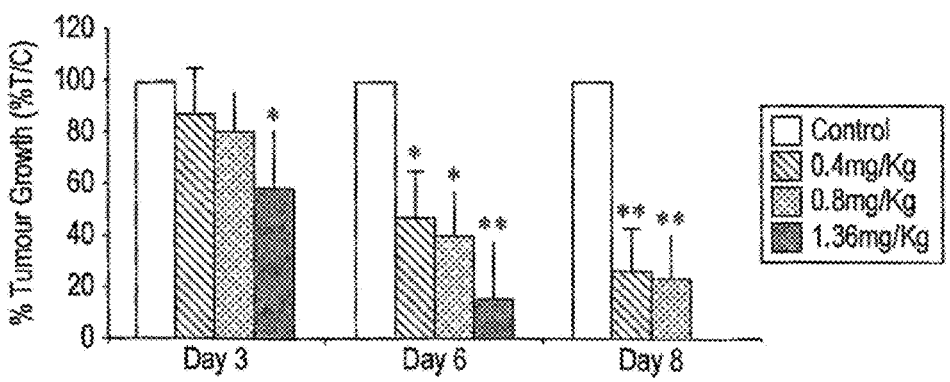
Figure 7:
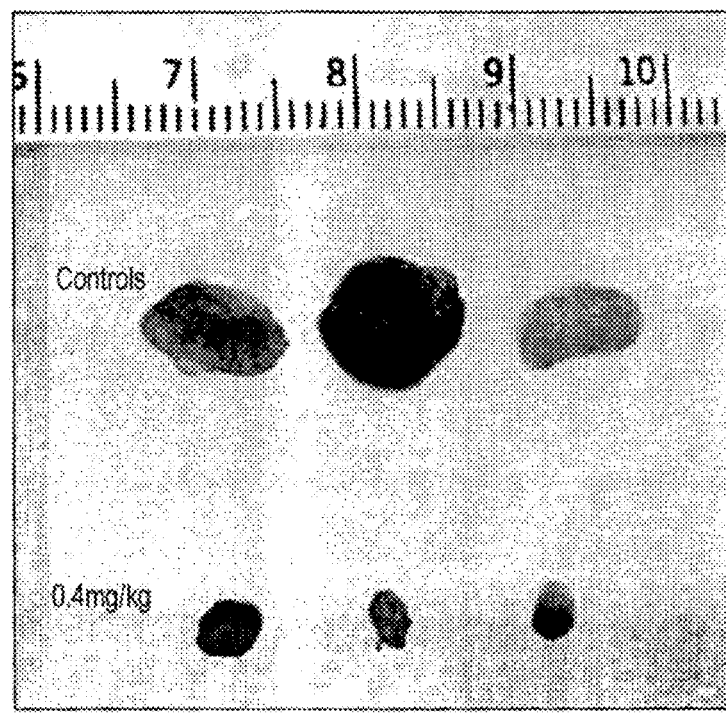
Figure 8:
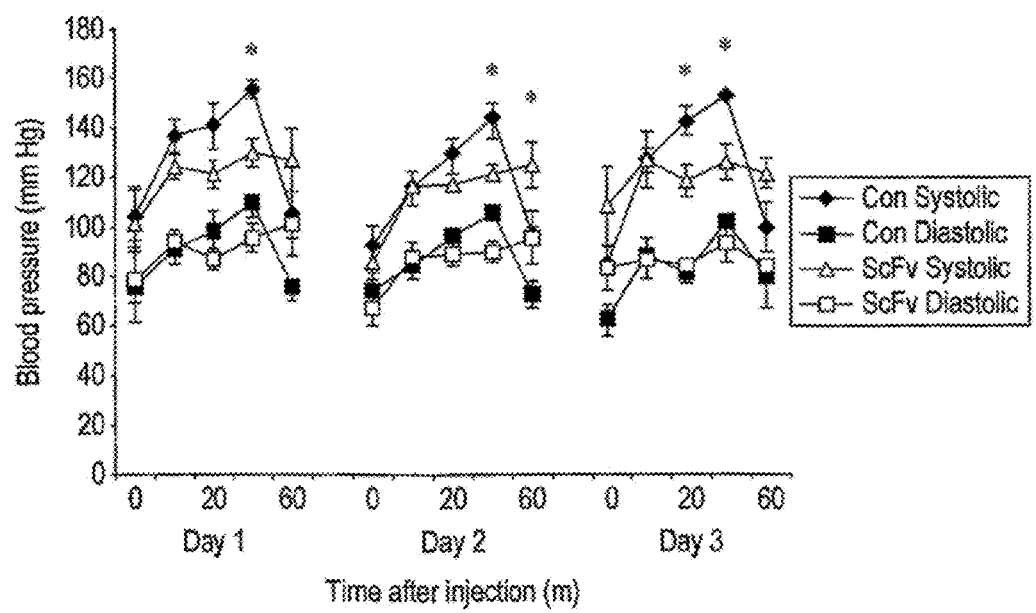
Figure 9A:
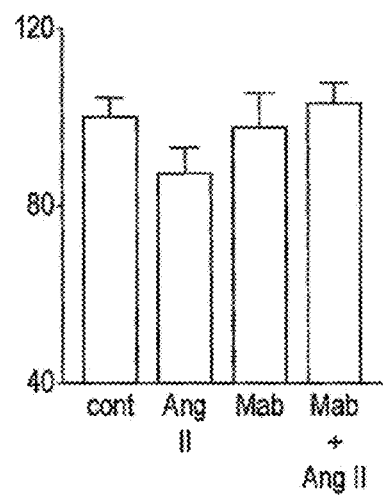
Figure 9B:
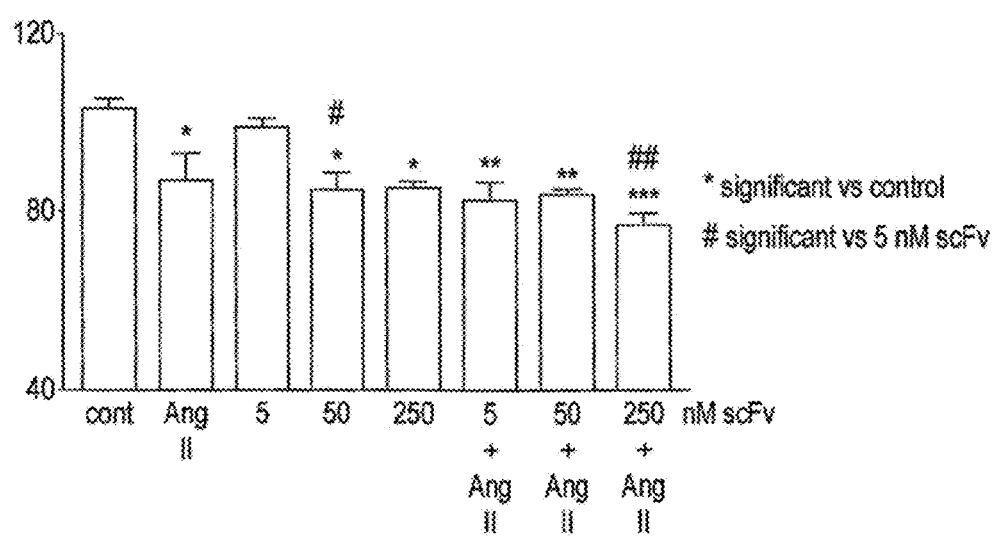
Figures 11B, 12A:
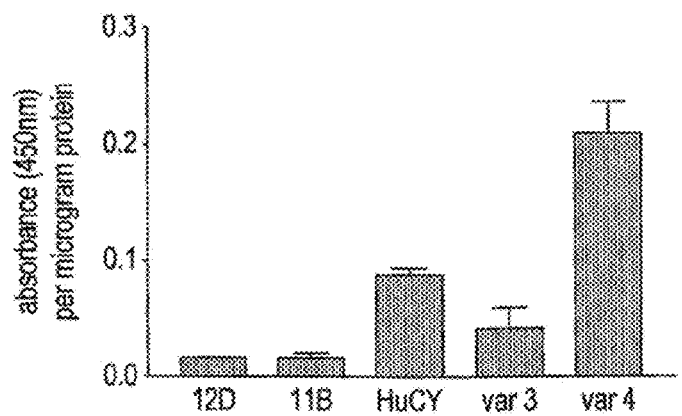
Figure 12B:
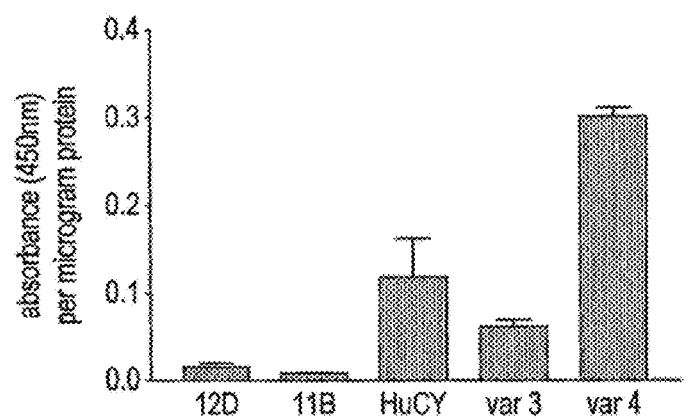
Figure 12C:
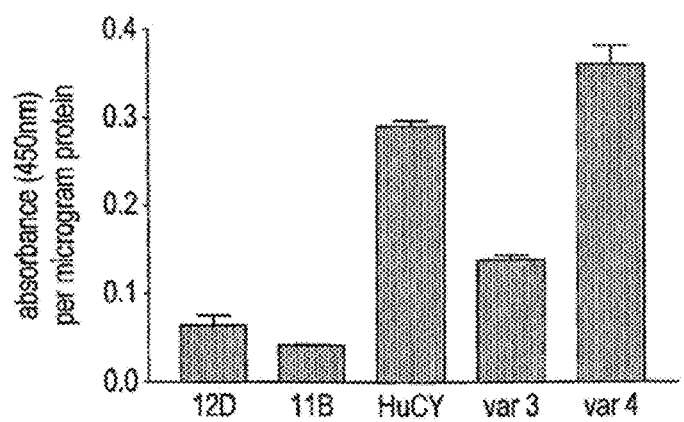
Figure 12D:
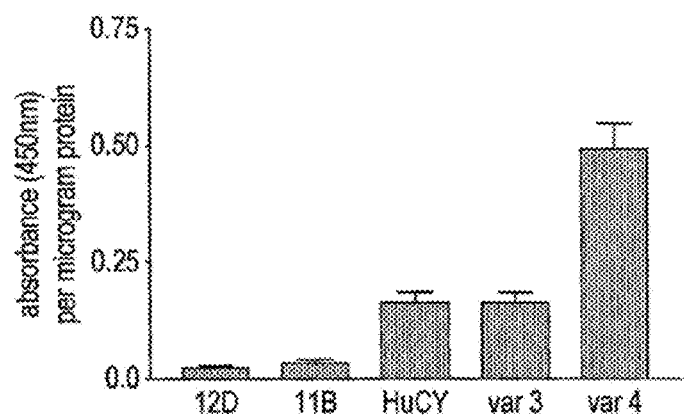

These were significantly stronger binders to the antigen in an ELISA plate assay during panning of the cDNA library derived from RNA from the original hybridoma cell population. The only change in the CDRs is in VHCDRH1. However, there is also one other difference between the two sequences at the N-terminus, KLQQ (SEQ ID NO:12) and QLQE (SEQ ID NO:13), respectively. An additional ten clones show other changes in CDRs and elsewhere in the structure (see FIG. 11), however in the ELISA assay these bound less strongly to the ELISA antigen plate.

The full sequences of clones 12D and 11B are aligned as shown in FIG. 10. The first 6 amino acids and last 8 amino acids are the leading sequences from the pCANTAB 5E vector, with the last 5 comprising part of the E-tag present in the expressed protein product used in these experiments.

Figure 14:
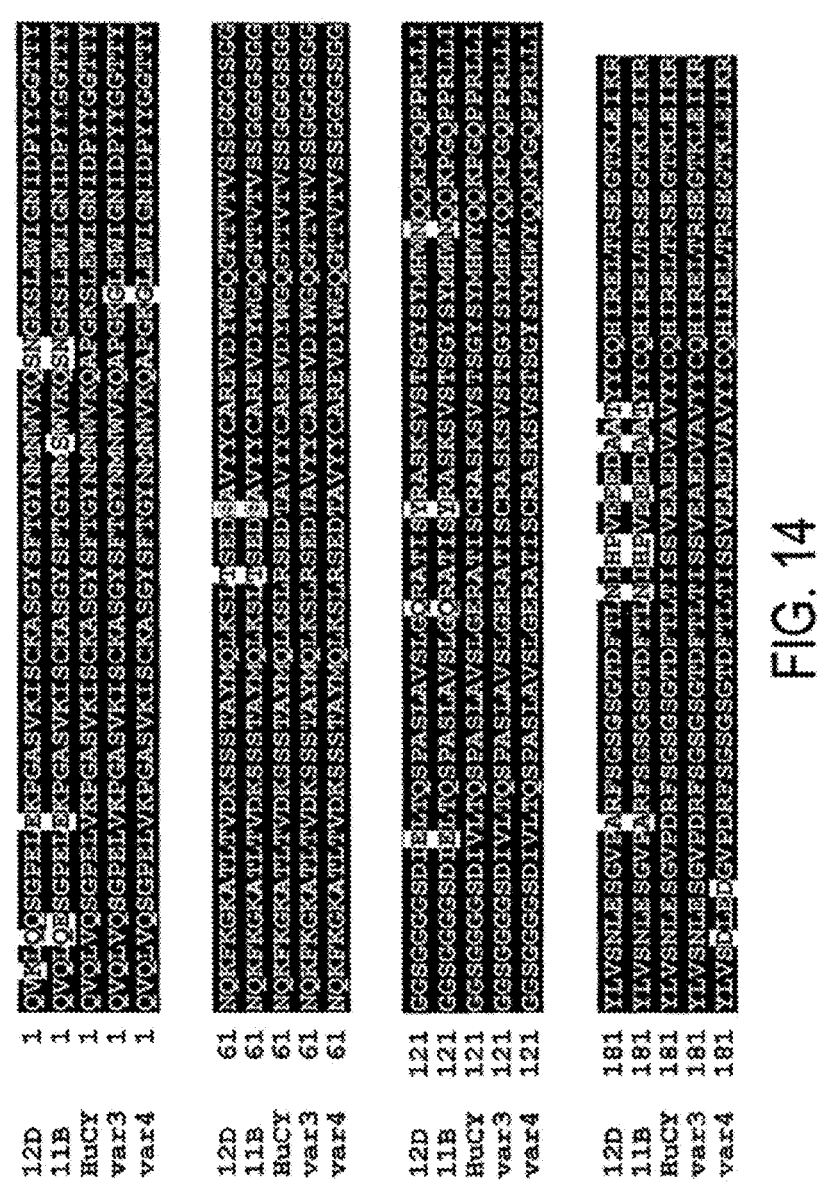

The effective amino acid sequences of clones 12D and 11B are shown in FIG. 14.

EXAMPLE 2

Activity Assays

The activity of the scFv R6313/G2 was studied in the following assays:
Cell Culture Procedures:

MCF-7, T47D and MDA-MB-231 breast cancer cells were obtained from The American Tissue Culture Collection (LGC Promochem, Teddington, UK). Rat aortic smooth muscle cells (RASMC) were developed from primary culture (Barker et al., 1996). MCF-7 cells were maintained in Minimal Essential Medium (MEM), T47D and MDA-MB-231 cells in RPMI 1640 medium, and RASMC were maintained in Dulbecco's Modified Eagle's Medium (DMEM). All media were supplemented with 2 mM L-glutamine, 10% fetal bovine serum (FBS), 50 U/ml penicillin and 0.05 mg/ml streptomycin. Cells were maintained at 37° C. in a humidified atmosphere (95% oxygen, 5% $CO_2$).

Cell Viability Assay:

Confluent cell monolayers were removed from tissue culture flasks using trypsin/EDTA. Cells ($15 \times 10^3$ per well) were seeded into 96 well tissue culture plates containing the appropriate medium for each cell line. After 24 hours, cells were treated with angiotensin II (100 nM) and R6313/G2 at a range of concentrations from 0.005 to 25 µM, or with losartan at a similar concentration range, and incubated for a further 48 hours. Cell viability was assessed by the ability of metabolically active cells to reduce 2,3-bis[2-Methoxy-4-nitro-5-sulphophenyl]-2H-tetrazolium-5-carboxyanilide inner salt (XTT) to the coloured formazan product. Absorbance was measured using a Multiskan Ascent microplate reader (Thermo Labsystem, Helsinki, Finland) at a wavelength of 450 nm and a reference wavelength of 630 nm. Each measurement was performed in triplicate. IC50s were calculated using a non-linear regression formula using GraphPad Prism v4.0 software (GraphPad Software Inc, San Diego Calif., USA).

Protein Extraction and Western Blotting:

Cells were grown in the presence or absence of angiotensin II (100 nmol/L) for 24 hours then washed three times in sterile PBS (pH 7.4), incubated for 5 minutes in lysis buffer (PBS pH 7.4, 1% NP-40/Triton X-100, 0.1% SDS and 0.5% sodium deoxycholate, with the protease inhibitors leupeptin 10 µg/ml, aprotinin 30 µg/ml and 0.1 mmol/L phenylmethylsulphonylfluoride), and harvested. Cell lysates were homogenised using an ultrasonicator (2×5 sec cycles; Bandelin Sonoplus, SLS, Hessle UK). After homogenisation the samples were centrifuged at 20,000 g for 10 minutes at 4° C. The supernatants were removed and stored at −80° C. Protein concentrations were estimated using the Bio-Rad protein assay (Bio-Rad Laboratories, Hemel Hempstead UK). For western blotting, samples containing 50 µg of total cell lysate were loaded on to a 10% SDS-polyacrylamide gel and subjected to electrophoresis. Proteins were transferred to Hybond-C membranes (Amersham Biosciences Ltd, Chalfont St Giles UK) in transfer buffer (39 mmol/L glycine, 48 mmol/L Tris-Base, 20% methanol, and 0.037% SDS), using a transBlot transfer apparatus (Bio-Rad Laboratories, Hemel Hempstead UK) at 120 mA for 1.5 hours at 4° C. Membranes were washed and then incubated in blocking buffer (1× Tris-Buffered Saline (TBS), 0.1% Tween 20 and 5% dried milk) for 1 hour at room temperature and subsequently washed three times for 10 minutes in washing buffer (1×TBS and 0.1% Tween 20). The membranes were incubated with polyclonal rabbit anti-AT1 receptor or anti-AT2 receptor antibodies at a dilution of 1:500 in blocking buffer. After overnight incubation at 4° C., the membranes were washed as described above and incubated with anti rabbit IgG secondary antibody (Amersham Biosciences) (1:2000) for 1 hour at room temperature. Additional washes were carried out and immune detection was performed by incubating the membranes for 1 minute in ECL western blotting detection reagent (Amersham Biosciences), and exposed to a Biomax chemiluminescence detection film (Kodak, Rochester N.Y., USA).

Apoptosis—Caspase-3/7 Activity:

Activation of caspases during apoptosis was determined using the Apo-ONE homogenous caspase-3/7 assay (Promega Corp, Southampton UK), according to the manufacturer's instructions. Briefly, cells were grown to 90% confluence and washed three times with sterile PBS. Cells were harvested using Trypsin/EDTA and counted. Cells ($10^4$ per well) were seeded into a 96 well plate and incubated with R6313/G2 at concentrations from 0.1 to 3 µM in the presence or absence of 100 nmol/L angiotensin II, total volume 150 µl, for 24 and 48 hours. After incubation, caspase-3/7 Z-DEVD- R110 substrate (100 µl) was added to each well. Blank wells contained reagent alone, and controls omitted the antibody and/or angiotensin II. Fluorescence was measured every 2 hours over an 8 hour period using a Fluostar Optima spectrofluorimeter (BMG Laboratories, Offenburg Germany), with an excitation wavelength of 485 nm and an emission wavelength of 535 nm.

Hollow Fiber Assay

Hollow Fiber procedures followed the method of Hollingshead. (Hollingshead et al Life Sci 57 131-41 (1995)).

Preparation of Hollow Fibers:

Polyvinylidene difluoride (PVDF) hollow fibers (500 kDa cut-off, 1 mm inner diameter; Spectrum Europe B.V., Breda, Netherlands) were flushed through with 70% ethanol using a blunt 21 gauge needle and 10 ml syringe. Fibers were then immersed in 70% ethanol for 72 hours, flushed through again with 70% ethanol, then distilled water, and then autoclaved at 131° C. Finally, before loading cell suspensions, fibers were flushed through with RPMI 1640 culture medium. Cells (MCF-7, T47D, and MDA-MB-231) were introduced into fibers at densities of 2.5 to $3.0 \times 10^6$ cells/ml. Fibers were then heat-sealed at 2 cm intervals and placed in Petri dishes containing 3 ml of the cell appropriate medium.

To test the efficacy of the method before use in vivo, cell-loaded fibers were incubated in vitro for 48 hours in the presence or absence of antibody at a range of concentrations from 0.33 µM to 33 µmol/L and angiotensin II (100 nmol/L).

In Vivo Hollow Fiber Assay:

Cell-loaded hollow fiber segments were incubated at 37° C. in culture medium overnight before implantation into pure strain 5-6 week old female balb/c nu/nu mice. Fibers were implanted into the animals under anaesthesia (2% Isofluorane). Three 2 cm fibers, each containing one of the cell lines MCF-7, T47D, or MDA-MB-231, were implanted at both subcutaneous (s.c.) and intraperitoneal (i.p.) sites into each animal. For i.p. implants, a small incision was made through the skin and musculature of the ventral abdominal wall. Fibers were placed into the peritoneal cavity and both incisions were closed with metallic suture clips (Harvard Instruments, Edenbridge UK). For s.c. implants, a small incision was made dorsally. The fibers were implanted to the left of the dorsal midline in a cranial direction. The small incision was closed with metallic suture clips.

Antibody Treatment:

Mice (n=5/group) with hollow fiber implants were treated with R6313/G2 (0.07 mg/kg (2.5 nmol/kg), and 0.7 mg/kg (25 nmol/kg) in 0.1 ml PBS, subcutaneously) twice per day for six days. Control animals (n=5) received vehicle alone. 24 hours after the last injection, animals were killed by cervical dislocation and the fibers were recovered and transferred to pre-warmed RPMI 1640 medium containing 20% FBS for 30 minutes.

Assessment of Tumour Cell Growth within Hollow Fibers:

Cell viability was measured using a modified MTT assay. Fibers were incubated in RPMI 1640 with 20% FBS containing 1 mg/ml MTT, and incubated at 37° C. under 95% $O_2$, 5% $CO_2$ for 4 hours. The reagent was aspirated, and 2 ml sterile filtered 2.5% protamine sulphate (0.9 g NaCl, 2.5 g protamine sulphate in 100 ml water) was added. Specimens were stored at 4° C. for a minimum of 24 hours in the dark to fix the formazan product. Fresh protamine sulphate (2.5%) was added and fibers were stored for a further 2 to 4 hours at 4° C. Each fiber was transferred to a well in a 24 well plate, cut in half and air-dried overnight, protected from light. Dimethyl sulphoxide (DMSO) (300 µl) was added to each well and the formazan product extracted. An aliquot (190 µl) from each well was transferred to a 96 well plate and absorbance read at 540 nm using a Multiskan Ascent photometric microplate reader (Thermo labsystem). Treated values were calculated as a percentage of the controls.

In Vivo Xenograft Assay:

Mice were injected s.c. on the right-flank, with 150 µl sterile PBS containing $7.5 \times 10^6$ MCF-7 cells. Tumour cells were allowed to grow for 4 weeks without hormone support, thereafter mice received weekly s.c. injections of 17β-oestradiol valerate (0.1 mg/Kg body weight), in sesame oil (Kasukabe et al., Breast Cancer Res. 7(6) R1097-110 (2005)) for a further 8 weeks. Animals were monitored daily for general health, and body weights were measured twice-weekly. Tumour size was measured 3 times per week with slide callipers, and volumes were calculated as $(L \times W^2)/2$, where L and W are the major and minor diameters, respectively. Once tumour volumes reached 150 to 200 mm$^3$, mice were randomized to treatment and control groups of 8 to 10 per group. Mice were treated by subcutaneous injections of R6313/G2 in sterile PBS (0.1 ml) at doses of 0.4 mg/kg (13 nmol/kg), 0.8 mg/kg (27 nmol/Kg), and 1.36 mg/kg (45.3 nmol/kg) body weight, twice per day for seven days. Control mice received sterile PBS. At the termination of the study, animals were sacrificed by cervical dislocation. Relative body weights (%) were calculated as (Wt/Wi)×100, where Wt is the body weight at any given time and Wi is the body weight at treatment initiation. Net tumour volume was calculated as Vt-Vi, where Vt is the tumour volume at any given time and Vi is the tumour volume at the start of treatment, and expressed as a percentage of Vi.

Rat Blood Pressure

Rats were chosen for this part of the study in view of their greater tractability in blood pressure assays. Female Wistar rats were first acclimatised to handling and the blood pressure equipment for 4-5 days before experimentation. Blood pressure in the conscious animals was determined using a Kent Scientific Corporation (Torrington Conn., USA) Coda 6+ tail cuff system in which the animals were held in warmed restrainers while blood pressures were assessed. Animals were first stabilised and their basal blood pressure taken before treatment. They were then briefly removed from the restrainers for sc injection of R6313/G2, 0.4 mg/kg in sterile PBS (0.1 ml). Controls received PBS alone. Blood pressures were then taken at intervals over a period of 1 hour, before restoring to cages. The procedures were repeated daily for 3 days.

Statistical Analysis:

All data were presented as means±SE. Statistical analysis was performed using one-way ANOVA. In the case of a significant result in the ANOVA, Student's t-test was used for the dose-response curves. A P value less than 0.05 was considered statistically significant.

Fluorimetric Invasion Assay

The method used is QCM™ Cell invasion assay (Chemicon Cat No. ECM555). This uses fluorimetric detection of cells which have broken through a reconstituted basement membrane matrix proteins (ECM) derived from the Engelbreth-Holm-Swam (EHS) mouse tumour (Repesh LA (1989) Invasion Metastasis 9: 192-208)

ECM-coated inserts were placed in 96-well plates and 100 µl of prewarmed serum-free medium added to the interior of the inserts in order to hydrate the ECM layer over 1-2 h at room temperature. Media was removed and 150 µl of serum free medium added to the wells of the 96-well plate housing the inserts. 100 µl of medium containing $10^5$ cells/per insert was then introduced. The plate was covered and incubated at 37 C in a 5% CO2/95% air humidified incubator for 24 h. After removing cells from inside the insert and rinsing with PBS, the insert was replaced into a 96-well plate containing Cell Detachment Solution and incubated at 37 C for 30 min. Cells that had invaded through the ECM to the bottom of the insert were, in this way, dislodged from the insert for subsequent lysis and measurement of fluorescence using a 480/520 filter set in a Fluostar Optima fluorimeter (BMG Labtech), according to manufacturer's instructions.

EXAMPLE 3

Design of Humanised Variants

The humanised variants were based on the murine sequence 12D described above. The amino acid substitutions were chosen by using a combination of previously published approaches together with a degree of intellectual latitude. Firstly, the murine scFv sequence was used to find the most homologous variable heavy and variable light chains in the NCBI database using a BLAST search. Secondly, the approach described by Padlan (*Molecular Immunology* 28(4/5) 489-498 (1991)) was used to indicate which amino acid residues were likely to be exposed (i.e. hydrophilic) or buried (hydrophobic) residues in the whole scFv molecule. Reference to the article by Padlan also provided options for which human germ-line amino acids could be used to substitute appropriately for murine residues and in this way generate a resurfaced scFv where, in general, replacement of these exposed murine residues would result in a less immunogenic whole scFv protein.

An additional two substitutions were included either side of one of the CDRs (hence CY) that were considered to be sensible to change because the human germ-line residues in these two positions were completely conserved across four subgroups of variable regions, in accordance with the disclosure of Padlan (supra).

All three of the humanised variants identified by this approach, HuCY, var3 and var4, bind to the peptide antigen (from the AT1-receptor N-terminal region) more strongly by ELISA than the two murine scFvs, 12D and 11B.

The murine scFv protein sequence was modified only in the framework regions contained within the variable heavy and variable light chains in order to produce the humanised variants HuCY and var3. However, the humanised variant var4 also has two further changes in CDR2 of the light chain.

The CDRs of the humanised variants are as follows:

```
HuCY and var3
VHCDR1:  GYSFTGYNMN            (SEQ ID NO: 2)

VHCDR2:  NIDPYYGGTTYNQKFKG     (SEQ ID NO: 3)

VHCDR3:  EVDY                  (SEQ ID NO: 4)

VLCDR1:  RASKSVSTSGYSYMH       (SEQ ID NO: 5)

VLCDR2:  LVSNLES               (SEQ ID NO: 6)

VLCDR3:  QHIRELTRSEG           (SEQ ID NO: 7)

var4
VHCDR1:  GYSFTGYNMS            (SEQ ID NO: 2)

VHCDR2:  NIDPYYGGTTYNQKFKG     (SEQ ID NO: 3)

VHCDR3:  EVDY                  (SEQ ID NO: 4)

VLCDR1:  RASKSVSTSGYSYMH       (SEQ ID NO: 5)
```

```
                    -continued
VLCDR2:  LVSDLED               (SEQ ID NO: 9)

VLCDR3:  QHIRELTRSEG           (SEQ ID NO: 7)
```

The sequences of clones 12D, 11B and of the humanised variants HuCY, variant 3 and variant 4 are shown in FIG. 14.

EXAMPLE 4

Activity Assays on Humanised Variants

The activity of the humanised variants was studied in the following assays:

Scfv Production and Purification for Comparative Binding Studies

All gene sequences were synthesised by Blue Heron Biotechnology (Bothell, Wash., USA) and integrated into a bacterial protein expression vector, upstream from a His-tag encoding sequence under the control of a T7lac promoter. The vector used included a periplasmic targeting leader sequence that is cleaved by signal peptidase after reaching the periplasmic space in the bacterial host. The skilled person will understand that other suitable vectors can also be used to produce the scFvs of the invention.

These constructs were transformed into Rosetta 2(DE3) competent cells (Merck-Novagen), according to manufacturer's protocol. Strains were routinely grown in LB broth or LB agar at 37° C., with 30 mg/liter kanamycin and 34 mg/liter chloramphenicol. Protein expression was carried out using 1 L bacterial cultures, grown for 24 hours in 2 L baffled flasks at 37° C. Protein production was then induced by the addition of IPTG, at a final concentration of 0.4 mM, for 5 hours at 25° C. Bacterial cell pellets were harvested in a Beckman Coulter Avanti J-30I centrifuge at 5000 g (rcf) for 20 minutes at 4° C., the cell pellet was then resuspended in 10 ml (per liter culture) in the following buffer, 0.4M Tris-HCL pH 8, 1 mM EDTA. The resulting cell pellets were then stored at −20° C. until purification.

To prepare the periplasmic fraction, the 1 L pellets were thawed and the following buffers added: 10 ml of 1M sucrose and 30 ml of 1/5 TES buffer (40 mM Tris-HCL pH 8, 0.1 mM EDTA, 0.1M sucrose and 5 mM $MgSO_4$). This cell suspension was then agitated on ice for 40 minutes, before centrifuging at 17418 g (rcf) for 20 minutes at 4° C. to separate the soluble periplasmic supernatant. This osmotic shock protocol is a modified version of a method given in the Novagen manual, taken from Ausubel et al., *Current Protocols in Molecular Biology*, John Wiley & Sons, New York (1989).

Periplasmic fractions were then filtered through 0.45 μM filters and applied to 1 ml pre-poured His-bind columns charged with $NiSO_4$ (Merck-Novagen). The purification was performed according to pET system manual instructions, using buffers supplied in the His-Bind Buffer kit (Merck-Novagen). The resulting eluate was buffer exchanged by passage through a PD-10 column (Pharmacia), which had previously been equilibrated in phosphate buffered saline pH 7.4 (PBS; Sigma P4417). The resulting scFv fraction was then concentrated using a 10 kDa molecular weight cut off spin concentrator (Amicon). The concentration of the scFv fraction in PBS was verified by running 10-15% SDS-polyacrylamide gels, performing Bio-Rad protein assays and recording a UV absorbance at 280 nm, the latter being converted to a concentration by dividing by the extinction coefficient (molar extinction coefficient divided by the molecular weight of the protein—~25.7 kDa) of 1.7.

IgM for comparative binding studies was purified as previously described for cellular invasion studies. The extinction coefficient used for IgM was 1.18 (Johnstone A, Thorpe R. *Immunochemistry in practice.* 2nd ed. Oxford: Blackwell Scientific Publications (1987)).

Testing of Antigen Binding Using ELISA

Enzyme-linked immunosorbant assays (ELISAs) were carried out in Maxisorp 96-well plates coated with Peptide antigen EDGIKRIQDDC-biotin (SEQ ID NO:14) (2-8 ug/ml in carbonate buffer pH 9.6) overnight at 4 or 37 C. The coated wells were blocked using 1% alkaline soluble casein (Blocking buffer) for 1 h at RT, then washed three times with PBS containing 0.1% v/v Tween 20. ScFv samples diluted between 1:1 to 1:100 in PBS-T were added and incubated for 1 h at RT before washing as before. A secondary HRP-conjugated anti-His-Tag antibody was then added (diluted 1:1000 in blocking buffer) for 1 h at RT. Wells were then washed three times in PBS-T then twice with PBS (without Tween 20). 100 µl of TMB substrate solution was added and colour was allowed to develop for 30 min, at which time 100 µl of 2M sulphuric acid was added to stop the reaction. Absorbance at 450 nm was read on a plate reading spectrophotometer. Protein concentrations were determined using an Eppendorf Biophotometer reading at 280 nm and using an extinction coefficient for the scFv of 1.7 as above. The results are shown in FIG. 12.

As can be seen from FIG. 12, there was increased binding to peptide antigen in resurfaced scFv (HuCY, var3 and var4) versus murine scFv (12D and 11B). It was unexpectedly observed that the changes made in the framework regions of the murine scFv resulted in a protein, HuCY, that bound to the antigenic peptide EDGIKRIQDDC-biotin (SEQ ID NO:1) 5-fold more avidly in an ELISA when compared with the same amount and purity of the murine scFv. Furthermore, the humanised variant var4 showed a 5-10 fold increase in binding to the antigen compared with the parent murine scFv. This is surprising since the one of the CDRs (VLCDR2) of var4was modified with respect to the parent murine scFv.

Figure 13:
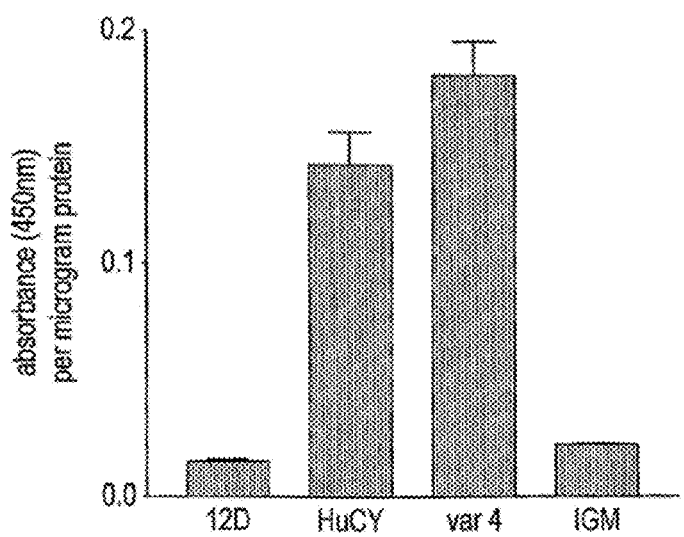
FIG. 13 shows an indirect comparison of murine scFv (12D) and engineered variant scFvs against purified IgM from original hybridoma. ELISA was carried out using an anti-His tag peroxidase secondary antibody conjugate (1:1000) for the scFvs, and an anti-IgM peroxidase secondary antibody conjugate (1:2500) for the hybridoma-derived IgM.

FIG. 13 shows an indirect comparison of murine scFv (12D) and engineered variant scFvs (HuCY and var4) against purified IgM from original hybridoma. As can be seen from FIG. 13, the variant scFvs had higher activity than the murine scFv.

Comparison of Binding Characteristics Using a Quartz Crystal Microbalance

Data were obtained comparing the characteristics of binding of the scFv variants and IgM to immobilised peptide antigen using the Attana 100 Quartz Crystal Microbalance. This involved use of a streptavidin (0.1 mg/ml)-coated biotin "chip" (gold-plated quartz crystal in an Attana 100 Biosensor (Quartz crystal microbalance (QCM)) (Attana AB, Stockholm, Sweden). Peptide antigen corresponding to that sequence used to raise the original murine hybridoma, biotinylated at the C-terminus, was then run across the chip at a concentration of 4 µg/ml to create a binding target for scFvs and IgM that were subsequently run across the surface of the QCM chip. Attester software (Attana, Sweden) was used to monitor changes in resonance frequency of the QCM chip in response to binding of a test antibody to the antigen. The magnitude of deflection in Hz over the period of sample injection of 100 s in Hz/second was determined for each antibody at a concentration of 9 µg/ml. The rate at which the antibody was then released from the QCM chip was also measured in Hz/second from the straight-line portion of the biosensor trace as antibody gradually departed from the chip and as the resonance frequency of the chip decreased. Running buffer was PBS containing 0.005% Tween 20 (PBST) and this was also used to make antibody dilutions to give a final protein concentration of 9 µg/ml in each case. The Attana 100 was set up with a 50 µl injection loop and was running with a constant pump speed of 20 µl/min. Samples and PBST buffer controls were injected over 100 seconds giving a sample volume across the chip of 33 µl. 100 mM (6.6 µl volume) phosphoric acid solution was used to regenerate the strepavidin-antigen surface between individual experimental sample runs.

The results are shown in FIG. 15. ScFvs 12D, var3 and var4 showed significantly greater increases in resonance frequency over the injection period compared with that for the IgM, whilst no significant differences were observed in the rate at which the antibody was released from the QCM chip under these experimental conditions.

The invention claimed is:

1. An antigen binding fragment of an antibody, wherein the antigen binding fragment specifically binds to a peptide comprising the amino acid sequence of EDGIKRIQDD (SEQ ID NO:1) and comprises an immunoglobulin $V_L$ domain linked to an immunoglobulin $V_H$ domain, wherein the $V_L$ domain comprises Complementary Determining Regions (CDRs) VLCDR1, VLCDR2 and VLCDR3, and the $V_H$ domain comprises Complementary Determining Regions (CDRs) VHCDR1, VHCDR2, VHCDR3, each consisting of the amino acid sequence as follows

```
VHCDR1 is GYSFTGYNMN;         (SEQ ID NO: 2)
VHCDR2 is NIDPYYGGTTYNQKFKG;  (SEQ ID NO: 3)
VHCDR3 is EVDY;               (SEQ ID NO: 4)
VLCDR1 is RASKSVSTSGYSYMH;    (SEQ ID NO: 5)
VLCDR2 is LVSNLES;            (SEQ ID NO: 6)
VLCDR3 is QHIRELTRSEG         (SEQ ID NO: 7).
```

2. The antigen binding fragment as claimed in claim 1 comprising a polypeptide comprising the amino acid sequence of SEQ ID.

3. A composition comprising the antigen binding fragment as claimed in claim 1 and angiotensin-II protein.

4. A pharmaceutical composition comprising the antigen binding fragment as claimed in claim 1.

5. A pharmaceutical composition comprising the antigen binding fragment as claimed in claim 1 and angiotensin-II protein.

\* \* \* \* \*

UNITED STATES PATENT AND TRADEMARK OFFICE
CERTIFICATE OF CORRECTION

| | | |
|---|---|---|
| PATENT NO. | : 8,487,082 B2 | Page 1 of 1 |
| APPLICATION NO. | : 12/867911 | |
| DATED | : July 16, 2013 | |
| INVENTOR(S) | : Vinson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 47 days.

Signed and Sealed this
Eighteenth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,487,082 B2
APPLICATION NO. : 12/867911
DATED : July 16, 2013
INVENTOR(S) : Gavin Paul Vinson et al.

Page 1 of 1

It is certified that error appears in the above-identified patent and that said Letters Patent is hereby corrected as shown below:

In the Claims

Claim 1, at Column 45, Line 58, please replace "Complementary" with --Complementarity--, therefor.

Claim 1, at Column 45, Line 60, please replace "Complementary" with --Complementarity--, therefor.

Claim 1, at Column 46, Line 57, please replace "LVSNLES" with --LVSNLED--, therefor.

Claim 1, at Column 46, Line 57, please replace "(SEQ ID NO:6)" with --(SEQ ID NO:9)--, therefor.

Claim 2, at Column 46, Line 62, please replace "SEQ ID" with --SEQ ID NO:29--, therefor.

Signed and Sealed this
Eleventh Day of November, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,487,082 B2  Page 1 of 1
APPLICATION NO. : 12/867911
DATED : July 16, 2013
INVENTOR(S) : Gavin Paul Vinson et al.

It is certified that error appears in the above-identified patent and that said Letters Patent is hereby corrected as shown below:

Claims

Claim 1, Column 46, Line 57, please replace "LVSNLED" with --LVSDLED--, therefor.

Signed and Sealed this
Fourth Day of August, 2015

Michelle K. Lee
*Director of the United States Patent and Trademark Office*

SEQUENCE LISTING

```
<160> NUMBER OF SEQ ID NOS: 29

<210> SEQ ID NO 1
<211> LENGTH: 10
<212> TYPE: PRT
<213> ORGANISM: Unknown
<220> FEATURE:
<223> OTHER INFORMATION: AT1 Receptor Epitope

<400> SEQUENCE: 1

Glu Asp Gly Ile Lys Arg Ile Gln Asp Asp
1               5                   10

<210> SEQ ID NO 2
<211> LENGTH: 10
<212> TYPE: PRT
<213> ORGANISM: Unknown
<220> FEATURE:
<223> OTHER INFORMATION: VHCDR1

<400> SEQUENCE: 2

Gly Tyr Ser Phe Thr Gly Tyr Asn Met Asn
1               5                   10
```

```
<210> SEQ ID NO 3
<211> LENGTH: 17
<212> TYPE: PRT
<213> ORGANISM: Unknown
<220> FEATURE:
<223> OTHER INFORMATION: VHCDR2

<400> SEQUENCE: 3

Asn Ile Asp Pro Tyr Tyr Gly Gly Thr Thr Tyr Asn Gln Lys Phe Lys
1               5                   10                  15

Gly

<210> SEQ ID NO 4
<211> LENGTH: 4
<212> TYPE: PRT
<213> ORGANISM: Unknown
<220> FEATURE:
<223> OTHER INFORMATION: VHCDR3

<400> SEQUENCE: 4

Glu Val Asp Tyr
1

<210> SEQ ID NO 5
<211> LENGTH: 15
<212> TYPE: PRT
<213> ORGANISM: Unknown
<220> FEATURE:
<223> OTHER INFORMATION: VLCDR1

<400> SEQUENCE: 5

Arg Ala Ser Lys Ser Val Ser Thr Ser Gly Tyr Ser Tyr Met His
1               5                   10                  15

<210> SEQ ID NO 6
<211> LENGTH: 7
<212> TYPE: PRT
<213> ORGANISM: Unknown
<220> FEATURE:
<223> OTHER INFORMATION: VLCDR2

<400> SEQUENCE: 6

Leu Val Ser Asn Leu Glu Ser
1               5

<210> SEQ ID NO 7
<211> LENGTH: 11
<212> TYPE: PRT
<213> ORGANISM: Unknown
<220> FEATURE:
<223> OTHER INFORMATION: VLCDR3

<400> SEQUENCE: 7

Gln His Ile Arg Glu Leu Thr Arg Ser Glu Gly
1               5                   10

<210> SEQ ID NO 8
<211> LENGTH: 10
<212> TYPE: PRT
<213> ORGANISM: Unknown
<220> FEATURE:
<223> OTHER INFORMATION: Alternative VHCDR1

<400> SEQUENCE: 8

Gly Tyr Ser Phe Thr Gly Tyr Asn Met Ser
1               5                   10
```

<210> SEQ ID NO 9
<211> LENGTH: 7
<212> TYPE: PRT
<213> ORGANISM: Unknown
<220> FEATURE:
<223> OTHER INFORMATION: Alternative VLCDR2

<400> SEQUENCE: 9

Leu Val Ser Asp Leu Glu Asp
1               5

<210> SEQ ID NO 10
<211> LENGTH: 6
<212> TYPE: PRT
<213> ORGANISM: Unknown
<220> FEATURE:
<223> OTHER INFORMATION: E-tag

<400> SEQUENCE: 10

Gly Ala Pro Val Pro Tyr
1               5

<210> SEQ ID NO 11
<211> LENGTH: 13
<212> TYPE: PRT
<213> ORGANISM: Unknown
<220> FEATURE:
<223> OTHER INFORMATION: Epitope tag

<400> SEQUENCE: 11

Gly Ala Pro Val Pro Tyr Pro Asp Pro Leu Glu Pro Arg
1               5                   10

<210> SEQ ID NO 12
<211> LENGTH: 4
<212> TYPE: PRT
<213> ORGANISM: Unknown
<220> FEATURE:
<223> OTHER INFORMATION: N-terminus

<400> SEQUENCE: 12

Lys Leu Gln Gln
1

<210> SEQ ID NO 13
<211> LENGTH: 4
<212> TYPE: PRT
<213> ORGANISM: Unknown
<220> FEATURE:
<223> OTHER INFORMATION: N-terminus

<400> SEQUENCE: 13

Gln Leu Gln Glu
1

<210> SEQ ID NO 14
<211> LENGTH: 11
<212> TYPE: PRT
<213> ORGANISM: Unknown
<220> FEATURE:
<223> OTHER INFORMATION: Peptide antigen

<400> SEQUENCE: 14

Glu Asp Gly Ile Lys Arg Ile Gln Asp Asp Cys
1               5                   10

```
<210> SEQ ID NO 15
<211> LENGTH: 255
<212> TYPE: PRT
<213> ORGANISM: Unknown
<220> FEATURE:
<223> OTHER INFORMATION: 12D

<400> SEQUENCE: 15

Tyr Ala Ala Gln Pro Ala Met Ala Gln Val Lys Leu Gln Gln Ser Gly
1               5                  10                  15

Pro Glu Leu Glu Lys Pro Gly Ala Ser Val Lys Ile Ser Cys Lys Ala
            20                  25                  30

Ser Gly Tyr Ser Phe Thr Gly Tyr Asn Met Asn Trp Val Lys Gln Ser
        35                  40                  45

Asn Gly Lys Ser Leu Glu Trp Ile Gly Asn Ile Asp Pro Tyr Tyr Gly
    50                  55                  60

Gly Thr Thr Tyr Asn Gln Lys Phe Lys Gly Lys Ala Thr Leu Thr Val
65                  70                  75                  80

Asp Lys Ser Ser Ser Thr Ala Tyr Met Gln Leu Lys Ser Leu Thr Ser
                85                  90                  95

Glu Asp Ser Ala Val Tyr Tyr Cys Ala Arg Glu Val Asp Tyr Trp Gly
            100                 105                 110

Gln Gly Thr Thr Val Thr Val Ser Gly Gly Gly Ser Gly Gly
        115                 120                 125

Gly Gly Ser Gly Gly Gly Ser Asp Ile Glu Leu Thr Gln Ser Pro
    130                 135                 140

Ala Ser Leu Ala Val Ser Leu Gly Gln Arg Ala Thr Ile Ser Tyr Arg
145                 150                 155                 160

Ala Ser Lys Ser Val Ser Thr Ser Gly Tyr Ser Tyr Met His Trp Asn
                165                 170                 175

Gln Gln Lys Pro Gly Gln Pro Pro Arg Leu Leu Ile Tyr Leu Val Ser
            180                 185                 190

Asn Leu Glu Ser Gly Val Pro Ala Arg Phe Ser Gly Ser Gly Ser Gly
        195                 200                 205

Thr Asp Phe Thr Leu Asn Ile His Pro Val Glu Glu Asp Ala Ala
    210                 215                 220

Thr Tyr Tyr Cys Gln His Ile Arg Glu Leu Thr Arg Ser Glu Gly Thr
225                 230                 235                 240

Lys Leu Glu Ile Lys Arg Ala Ala Ala Gly Ala Pro Val Pro Tyr
                245                 250                 255

<210> SEQ ID NO 16
<211> LENGTH: 255
<212> TYPE: PRT
<213> ORGANISM: Unknown
<220> FEATURE:
<223> OTHER INFORMATION: 11B

<400> SEQUENCE: 16

Tyr Ala Ala Gln Pro Ala Met Ala Gln Val Gln Leu Gln Glu Ser Gly
1               5                  10                  15

Pro Glu Leu Glu Lys Pro Gly Ala Ser Val Lys Ile Ser Cys Lys Ala
            20                  25                  30

Ser Gly Tyr Ser Phe Thr Gly Tyr Asn Met Ser Trp Val Lys Gln Ser
        35                  40                  45

Asn Gly Lys Ser Leu Glu Trp Ile Gly Asn Ile Asp Pro Tyr Tyr Gly
    50                  55                  60

Gly Thr Thr Tyr Asn Gln Lys Phe Lys Gly Lys Ala Thr Leu Thr Val
```

```
                65                  70                  75                  80
Asp Lys Ser Ser Ser Thr Ala Tyr Met Gln Leu Lys Ser Leu Thr Ser
                    85                  90                  95
Glu Asp Ser Ala Val Tyr Tyr Cys Ala Arg Glu Val Asp Tyr Trp Gly
                100                 105                 110
Gln Gly Thr Thr Val Thr Val Ser Gly Gly Gly Ser Gly Gly
                115                 120                 125
Gly Gly Ser Gly Gly Gly Ser Asp Ile Glu Leu Thr Gln Ser Pro
            130                 135                 140
Ala Ser Leu Ala Val Ser Leu Gly Gln Arg Ala Thr Ile Ser Tyr Arg
145                 150                 155                 160
Ala Ser Lys Ser Val Ser Thr Ser Gly Tyr Ser Tyr Met His Trp Asn
                165                 170                 175
Gln Gln Lys Pro Gly Gln Pro Pro Arg Leu Leu Ile Tyr Leu Val Ser
                180                 185                 190
Asn Leu Glu Ser Gly Val Pro Ala Arg Phe Ser Gly Ser Gly Ser Gly
            195                 200                 205
Thr Asp Phe Thr Leu Asn Ile His Pro Val Glu Glu Asp Ala Ala
210                 215                 220
Thr Tyr Tyr Cys Gln His Ile Arg Glu Leu Thr Arg Ser Glu Gly Thr
225                 230                 235                 240
Lys Leu Glu Ile Lys Arg Ala Ala Ala Gly Ala Pro Val Pro Tyr
                245                 250                 255

<210> SEQ ID NO 17
<211> LENGTH: 255
<212> TYPE: PRT
<213> ORGANISM: Unknown
<220> FEATURE:
<223> OTHER INFORMATION: 10D

<400> SEQUENCE: 17

Tyr Ala Ala Gln Pro Ala Met Ala Gln Val Lys Leu Gln Gln Ser Gly
1               5                   10                  15
Pro Glu Leu Glu Lys Pro Gly Ala Ser Val Lys Ile Ser Cys Lys Ala
            20                  25                  30
Ser Gly Tyr Ser Phe Thr Gly Tyr Asn Met Asn Trp Val Lys Gln Ser
                35                  40                  45
Asn Gly Lys Ser Leu Glu Trp Ile Gly Asn Ile Asp Pro Tyr Tyr Gly
        50                  55                  60
Gly Thr Thr Tyr Asn Gln Lys Phe Lys Gly Lys Ala Thr Leu Thr Val
65                  70                  75                  80
Asp Lys Ser Ser Ser Thr Ala Tyr Met Gln Leu Lys Ser Leu Thr Ser
                85                  90                  95
Glu Asp Ser Ala Val Tyr Tyr Cys Ala Arg Glu Val Asp Tyr Trp Gly
                100                 105                 110
Gln Gly Thr Thr Val Thr Val Ser Ser Gly Gly Gly Gly Ser Gly Gly
            115                 120                 125
Gly Gly Ser Gly Gly Gly Gly Ser Asp Ile Val Leu Thr Gln Ser Pro
            130                 135                 140
Ala Ser Leu Ala Val Ser Leu Gly Gln Arg Ala Thr Ile Ser Tyr Arg
145                 150                 155                 160
Ala Ser Lys Ser Ile Ser Thr Ser Gly Tyr Ser Tyr Met His Trp Asn
                165                 170                 175
Gln Gln Lys Pro Gly Gln Pro Pro Arg Leu Leu Ile Tyr Leu Val Ser
                180                 185                 190
```

-continued

Asn Leu Glu Ser Gly Val Pro Ala Arg Phe Ser Gly Ser Gly Ser Gly
            195                 200                 205

Thr Asp Phe Thr Leu Asn Ile His Pro Val Glu Glu Glu Asp Ala Ala
    210                 215                 220

Thr Tyr Tyr Cys Gln His Ile Arg Glu Leu Thr Arg Ser Glu Gly Thr
225                 230                 235                 240

Lys Leu Glu Leu Lys Arg Ala Ala Ala Gly Ala Pro Val Pro Tyr
                245                 250                 255

<210> SEQ ID NO 18
<211> LENGTH: 255
<212> TYPE: PRT
<213> ORGANISM: Unknown
<220> FEATURE:
<223> OTHER INFORMATION: 10E

<400> SEQUENCE: 18

Tyr Ala Ala Gln Pro Ala Met Ala Gln Val Gln Leu Gln Glu Ser Gly
1               5                   10                  15

Pro Glu Leu Glu Lys Pro Gly Ala Ser Val Lys Ile Ser Cys Lys Ala
            20                  25                  30

Ser Gly Tyr Ser Phe Thr Gly Tyr Asn Met Asn Trp Val Lys Gln Ser
        35                  40                  45

Asn Gly Lys Ser Leu Glu Trp Ile Gly Asn Ile Asp Pro Tyr Tyr Gly
    50                  55                  60

Gly Thr Thr Tyr Asn Gln Lys Phe Lys Gly Lys Ala Thr Leu Thr Val
65                  70                  75                  80

Asp Lys Ser Ser Ser Thr Ala Tyr Met Gln Leu Lys Ser Leu Thr Ser
                85                  90                  95

Glu Asp Ser Ala Val Tyr Tyr Cys Ala Arg Glu Val Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Asp Ile Glu Leu Thr Gln Ser Pro
    130                 135                 140

Ala Ser Leu Ala Val Ser Leu Gly Gln Arg Ala Thr Ile Ser Tyr Arg
145                 150                 155                 160

Ala Ser Lys Ser Val Ser Thr Ser Gly Tyr Ser Tyr Met His Trp Asn
                165                 170                 175

Gln Gln Lys Pro Gly Gln Pro Pro Arg Leu Leu Ile Tyr Leu Val Ser
            180                 185                 190

Asn Leu Glu Ser Gly Val Pro Ala Arg Phe Ser Gly Ser Gly Ser Gly
        195                 200                 205

Thr Asp Phe Thr Leu Asn Ile His Pro Val Glu Glu Glu Asp Ala Ala
    210                 215                 220

Thr Tyr Tyr Cys Gln His Ile Arg Glu Leu Thr Arg Ser Glu Gly Thr
225                 230                 235                 240

Lys Leu Glu Ile Lys Arg Ala Ala Ala Gly Ala Pro Val Pro Tyr
                245                 250                 255

<210> SEQ ID NO 19
<211> LENGTH: 255
<212> TYPE: PRT
<213> ORGANISM: Unknown
<220> FEATURE:
<223> OTHER INFORMATION: 4F

<400> SEQUENCE: 19

Tyr Ala Ala Gln Pro Ala Met Ala Gln Val Lys Leu Gln Gln Ser Gly
1               5                   10                  15

Pro Glu Leu Glu Lys Pro Gly Ala Ser Val Lys Ile Ser Cys Lys Ala
            20                  25                  30

Ser Gly Tyr Ser Phe Thr Gly Tyr Asn Met Asn Trp Val Lys Gln Ser
        35                  40                  45

Asn Gly Lys Ser Leu Glu Trp Ile Gly Asn Ile Asp Pro Tyr Tyr Gly
    50                  55                  60

Gly Thr Thr Tyr Asn Gln Lys Phe Lys Gly Lys Ala Thr Leu Thr Val
65                  70                  75                  80

Asp Lys Ser Ser Ser Thr Ala Tyr Met Gln Leu Lys Ser Leu Thr Ser
            85                  90                  95

Glu Asp Ser Ala Val Tyr Tyr Cys Ala Arg Glu Val Asp Tyr Trp Gly
            100                 105                 110

Gln Gly Thr Thr Val Thr Val Ser Ser Gly Gly Gly Ser Gly Gly
            115                 120                 125

Gly Gly Ser Gly Gly Gly Leu Asp Ile Glu Leu Thr Gln Ser Pro
    130                 135                 140

Ala Ser Leu Ala Val Ser Leu Gly Gln Arg Ala Thr Ile Ser Tyr Arg
145                 150                 155                 160

Ala Ser Lys Ser Val Ser Thr Ser Gly Tyr Ser Tyr Met His Trp Asn
                165                 170                 175

Gln Gln Lys Pro Gly Gln Pro Pro Arg Leu Leu Ile Tyr Leu Val Ser
            180                 185                 190

Asn Leu Glu Ser Gly Val Pro Ala Arg Phe Ser Gly Ser Gly Ser Gly
        195                 200                 205

Thr Asp Phe Thr Leu Asn Ile His Pro Val Glu Glu Asp Ala Ala
    210                 215                 220

Thr Tyr Tyr Cys Gln His Ile Arg Glu Leu Thr Arg Ser Glu Gly Thr
225                 230                 235                 240

Lys Leu Glu Ile Lys Arg Ala Ala Ala Gly Ala Pro Val Pro Tyr
            245                 250                 255

<210> SEQ ID NO 20
<211> LENGTH: 255
<212> TYPE: PRT
<213> ORGANISM: Unknown
<220> FEATURE:
<223> OTHER INFORMATION: 6C

<400> SEQUENCE: 20

Tyr Ala Ala Gln Pro Ala Met Ala Gln Val Gln Ala Gln Glu Ser Gly
1               5                   10                  15

Pro Glu Leu Glu Lys Pro Gly Ala Ser Val Lys Ile Ser Cys Lys Ala
            20                  25                  30

Ser Gly Tyr Ser Phe Thr Gly Tyr Asn Met Asn Trp Val Lys Gln Ser
        35                  40                  45

Asn Gly Lys Ser Leu Glu Trp Ile Gly Asn Ile Asp Pro Tyr Tyr Gly
    50                  55                  60

Gly Thr Thr Tyr Asn Gln Lys Phe Lys Gly Lys Ala Thr Leu Thr Val
65                  70                  75                  80

Asp Lys Ser Ser Ser Thr Ala Tyr Met Gln Leu Lys Ser Leu Thr Ser
            85                  90                  95

Glu Asp Ser Ala Val Tyr Tyr Cys Ala Arg Glu Val Asp Tyr Trp Gly
            100                 105                 110

Gln Gly Thr Thr Val Thr Val Ser Ser Gly Gly Gly Ser Gly Gly
            115                 120                 125

Gly Gly Ser Gly Gly Gly Ser Asp Ile Glu Leu Thr Gln Ser Pro
        130                 135                 140

Ala Ser Leu Ala Val Ser Leu Gly Gln Arg Ala Thr Ile Ser Tyr Arg
145                 150                 155                 160

Ala Ser Lys Ser Val Ser Thr Ser Gly Tyr Ser Tyr Met His Trp Asn
                165                 170                 175

Gln Gln Lys Pro Gly Gln Pro Pro Arg Leu Leu Ile Tyr Leu Val Ser
                180                 185                 190

Asn Leu Glu Ser Gly Val Pro Ala Arg Phe Ser Gly Ser Gly Ser Gly
                195                 200                 205

Thr Asp Phe Thr Leu Asn Ile His Pro Val Glu Glu Asp Ala Ala
210                 215                 220

Thr Tyr Tyr Cys Gln His Ile Arg Glu Leu Thr Arg Ser Glu Gly Thr
225                 230                 235                 240

Lys Leu Glu Ile Lys Arg Ala Ala Gly Ala Pro Val Pro Tyr
                245                 250                 255

<210> SEQ ID NO 21
<211> LENGTH: 255
<212> TYPE: PRT
<213> ORGANISM: Unknown
<220> FEATURE:
<223> OTHER INFORMATION: 6E

<400> SEQUENCE: 21

Tyr Ala Ala Gln Pro Ala Met Ala Gln Val Lys Leu Arg Glu Ser Gly
1               5                   10                  15

Pro Glu Leu Glu Lys Pro Gly Ala Ser Val Lys Ile Ser Cys Lys Ala
                20                  25                  30

Ser Gly Tyr Ser Phe Thr Gly Tyr Asn Met Asn Trp Val Lys Gln Ser
            35                  40                  45

Asn Gly Lys Ser Leu Glu Trp Ile Gly Asn Ile Asp Pro Tyr Tyr Gly
        50                  55                  60

Gly Thr Thr Tyr Asn Gln Lys Phe Lys Gly Lys Ala Thr Leu Thr Val
65                  70                  75                  80

Asp Lys Ser Ser Ser Thr Ala Tyr Met Gln Leu Lys Ser Leu Thr Ser
                85                  90                  95

Glu Asp Ser Ala Val Tyr Tyr Cys Ala Arg Glu Val Asp Tyr Trp Gly
                100                 105                 110

Gln Gly Thr Thr Val Thr Val Ser Ser Gly Gly Gly Ser Gly Gly
            115                 120                 125

Gly Gly Ser Gly Gly Gly Ser Asp Ile Glu Leu Thr Gln Ser Pro
        130                 135                 140

Ala Ser Leu Ala Val Ser Leu Gly Gln Arg Ala Thr Ile Ser Tyr Arg
145                 150                 155                 160

Ala Ser Lys Ser Val Ser Thr Ser Gly Tyr Ser Tyr Met His Trp Asn
                165                 170                 175

Gln Gln Lys Pro Gly Gln Pro Pro Arg Leu Leu Ile Tyr Leu Val Ser
                180                 185                 190

Asn Leu Glu Ser Gly Val Pro Ala Arg Phe Ser Gly Ser Gly Ser Gly
                195                 200                 205

Thr Asp Phe Thr Leu Asn Ile His Pro Val Glu Glu Asp Ala Ala
210                 215                 220

Thr Tyr Tyr Cys Gln His Ile Arg Glu Leu Thr Arg Ser Glu Gly Thr

```
225                 230                 235                 240

Lys Leu Glu Ile Lys Arg Ala Ala Ala Gly Ala Pro Val Pro Tyr
                245                 250                 255

<210> SEQ ID NO 22
<211> LENGTH: 255
<212> TYPE: PRT
<213> ORGANISM: Unknown
<220> FEATURE:
<223> OTHER INFORMATION: 7F

<400> SEQUENCE: 22

Tyr Ala Ala Gln Pro Ala Met Ala Gln Val Gln Leu Arg Glu Ser Gly
1               5                   10                  15

Pro Glu Leu Glu Lys Pro Gly Ala Ser Val Lys Ile Ser Cys Lys Ala
            20                  25                  30

Ser Gly Tyr Ser Phe Thr Gly Tyr Asn Met Asn Trp Val Lys Gln Ser
        35                  40                  45

Asn Gly Lys Ser Leu Glu Trp Ile Gly Asn Ile Asp Pro Tyr Tyr Gly
    50                  55                  60

Gly Thr Thr Tyr Asn Gln Lys Phe Lys Gly Lys Ala Thr Leu Thr Val
65                  70                  75                  80

Asp Arg Ser Ser Ser Thr Ala Tyr Met Gln Leu Lys Ser Leu Thr Ser
                85                  90                  95

Glu Asp Ser Ala Val Tyr Tyr Cys Ala Arg Glu Val Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Asp Ile Glu Leu Thr Gln Ser Pro
    130                 135                 140

Ala Ser Leu Ala Val Ser Leu Gly Gln Arg Ala Thr Ile Ser Tyr Arg
145                 150                 155                 160

Ala Ser Lys Ser Val Ser Thr Ser Gly Tyr Ser Tyr Met His Trp Asn
                165                 170                 175

Gln Gln Lys Pro Gly Gln Pro Pro Arg Leu Leu Ile Tyr Leu Val Ser
            180                 185                 190

Ser Leu Glu Ser Gly Val Pro Ala Arg Phe Ser Gly Ser Gly Ser Gly
        195                 200                 205

Thr Asp Phe Thr Leu Asn Ile His Pro Val Glu Glu Glu Asp Ala Ala
    210                 215                 220

Thr Tyr Tyr Cys Gln His Ile Arg Glu Leu Thr Arg Ser Glu Gly Thr
225                 230                 235                 240

Lys Leu Glu Ile Lys Arg Ala Ala Ala Gly Ala Pro Val Pro Tyr
                245                 250                 255

<210> SEQ ID NO 23
<211> LENGTH: 255
<212> TYPE: PRT
<213> ORGANISM: Unknown
<220> FEATURE:
<223> OTHER INFORMATION: 8B

<400> SEQUENCE: 23

Tyr Ala Ala Gln Pro Ala Met Ala Gln Val Lys Leu Gln Glu Ser Gly
1               5                   10                  15

Pro Glu Leu Glu Lys Pro Gly Ala Ser Val Lys Ile Ser Cys Lys Ala
            20                  25                  30

Ser Gly Tyr Ser Phe Thr Gly Tyr Asn Met Asn Trp Val Lys Gln Ser
```

```
                35                  40                  45
Asn Gly Lys Ser Leu Glu Trp Ile Gly Asn Ile Asp Pro Tyr Tyr Gly
 50                  55                  60
Gly Thr Thr Tyr Asn Gln Lys Phe Lys Gly Lys Ala Thr Leu Thr Val
 65                  70                  75                  80
Asp Lys Ser Ser Ser Thr Ala Tyr Met Gln Leu Lys Ser Leu Thr Ser
                 85                  90                  95
Glu Asp Ser Ala Val Tyr Tyr Cys Ala Arg Glu Val Asp Tyr Trp Gly
                100                 105                 110
Gln Gly Thr Thr Val Thr Val Ser Ser Gly Gly Gly Ser Gly Gly
                115                 120                 125
Gly Gly Ser Gly Gly Gly Ser Asp Ile Glu Leu Thr Gln Ser Pro
            130                 135                 140
Ala Ser Leu Ala Val Ser Leu Gly Gln Arg Ala Thr Ile Ser Tyr Arg
145                 150                 155                 160
Ala Ser Lys Ser Val Ser Thr Ser Gly Tyr Ser Tyr Met His Trp Asn
                165                 170                 175
Gln Gln Lys Pro Gly Gln Pro Pro Arg Leu Leu Ile Tyr Leu Val Ser
                180                 185                 190
Asn Leu Glu Ser Gly Val Pro Ala Arg Phe Ser Gly Ser Gly Ser Gly
                195                 200                 205
Thr Asp Phe Thr Leu Asn Ile His Pro Val Glu Glu Asp Ala Ala
    210                 215                 220
Thr Tyr Tyr Cys Gln His Ile Arg Glu Leu Thr Arg Ser Glu Gly Thr
225                 230                 235                 240
Lys Leu Glu Ile Lys Arg Ala Ala Ala Gly Ala Pro Val Pro Tyr
                245                 250                 255

<210> SEQ ID NO 24
<211> LENGTH: 255
<212> TYPE: PRT
<213> ORGANISM: Unknown
<220> FEATURE:
<223> OTHER INFORMATION: 8C

<400> SEQUENCE: 24

Tyr Ala Ala Gln Pro Ala Met Ala Gln Val Gln Leu Gln Glu Ser Gly
 1               5                  10                  15
Pro Glu Leu Glu Lys Pro Gly Ala Ser Val Lys Ile Ser Arg Lys Ala
                20                  25                  30
Ser Gly Tyr Ser Phe Thr Gly Tyr Asn Met Asn Trp Val Lys Gln Ser
            35                  40                  45
Asn Gly Lys Ser Leu Glu Trp Ile Gly Asn Ile Asp Pro Tyr Tyr Gly
 50                  55                  60
Gly Thr Thr Tyr Asn Gln Lys Phe Lys Gly Lys Ala Thr Leu Thr Val
 65                  70                  75                  80
Asp Lys Ser Ser Ser Thr Ala Tyr Met Gln Leu Lys Ser Leu Thr Ser
                 85                  90                  95
Glu Asp Ser Ala Val Tyr Tyr Cys Ala Arg Glu Val Asp Tyr Trp Gly
                100                 105                 110
Gln Gly Thr Thr Val Thr Val Ser Ser Gly Gly Gly Gly Ser Gly Gly
                115                 120                 125
Gly Gly Ser Gly Gly Gly Gly Ser Asp Ile Val Leu Thr Gln Ser Pro
            130                 135                 140
Ala Ser Leu Ala Val Ser Leu Gly Gln Arg Ala Thr Ile Ser Tyr Arg
145                 150                 155                 160
```

```
Ala Ser Lys Ser Val Ser Thr Ser Gly Tyr Ser Tyr Met His Trp Asn
            165                 170                 175

Gln Gln Lys Pro Gly Gln Pro Arg Leu Leu Ile Tyr Leu Val Ser
        180                 185                 190

Asn Leu Glu Ser Gly Val Pro Ala Arg Phe Ser Gly Ser Gly Ser Gly
            195                 200                 205

Thr Asp Phe Thr Leu Asn Ile His Pro Val Glu Glu Asp Ala Ala
210                 215                 220

Thr Tyr Tyr Cys Gln His Ile Arg Glu Leu Thr Arg Ser Glu Gly Thr
225                 230                 235                 240

Lys Leu Glu Ile Lys Arg Ala Ala Ala Gly Ala Pro Val Pro Tyr
                245                 250                 255

<210> SEQ ID NO 25
<211> LENGTH: 255
<212> TYPE: PRT
<213> ORGANISM: Unknown
<220> FEATURE:
<223> OTHER INFORMATION: 8D

<400> SEQUENCE: 25

Tyr Ala Ala Gln Pro Ala Met Ala Gln Val Gln Leu Gln Glu Ser Gly
1               5                   10                  15

Pro Glu Leu Glu Lys Pro Gly Ala Ser Val Lys Ile Ser Cys Lys Ala
            20                  25                  30

Ser Gly Tyr Ser Phe Thr Gly Tyr Asn Met Ser Trp Val Lys Gln Ser
        35                  40                  45

Asn Gly Lys Ser Leu Glu Trp Ile Gly Asn Ile Asp Pro Tyr Tyr Gly
    50                  55                  60

Gly Thr Thr Tyr Asn Gln Lys Phe Lys Gly Lys Ala Thr Leu Thr Val
65                  70                  75                  80

Asp Lys Ser Ser Ser Thr Ala Tyr Met Gln Leu Lys Ser Leu Thr Ser
                85                  90                  95

Glu Asp Ser Ala Val Tyr Tyr Cys Ala Arg Glu Val Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Asp Ile Glu Leu Thr Gln Ser Pro
    130                 135                 140

Ala Ser Leu Ala Val Ser Leu Gly Gln Arg Ala Thr Ile Ser Tyr Arg
145                 150                 155                 160

Ala Ser Lys Ser Val Ser Thr Ser Gly Tyr Ser Tyr Met His Trp Asn
                165                 170                 175

Gln Gln Lys Pro Gly Gln Pro Arg Leu Leu Ile Tyr Leu Val Ser
            180                 185                 190

Asn Leu Gly Ser Gly Val Pro Ala Arg Phe Ser Gly Ser Gly Ser Gly
        195                 200                 205

Thr Asp Phe Thr Leu Asn Ile His Pro Val Glu Glu Asp Ala Ala
    210                 215                 220

Thr Tyr Tyr Cys Gln His Ile Arg Glu Leu Thr Arg Ser Glu Gly Thr
225                 230                 235                 240

Lys Leu Glu Ile Lys Arg Ala Ala Ala Gly Ala Pro Val Pro Tyr
                245                 250                 255

<210> SEQ ID NO 26
<211> LENGTH: 255
```

```
<212> TYPE: PRT
<213> ORGANISM: Unknown
<220> FEATURE:
<223> OTHER INFORMATION: 8E

<400> SEQUENCE: 26

Tyr Ala Ala Gln Pro Ala Met Ala Gln Val Lys Leu Gln Gln Ser Gly
1               5                   10                  15

Pro Glu Leu Glu Lys Pro Gly Ala Ser Val Lys Ile Ser Cys Lys Ala
            20                  25                  30

Ser Gly Tyr Ser Phe Thr Gly Tyr Asn Met Asn Trp Val Lys Gln Ser
        35                  40                  45

Asn Gly Lys Ser Leu Glu Trp Ile Gly Asn Ile Asp Pro Tyr Tyr Gly
    50                  55                  60

Gly Thr Thr Tyr Asn Gln Lys Phe Lys Gly Lys Ala Thr Leu Thr Val
65                  70                  75                  80

Asp Lys Ser Ser Ser Thr Ala Tyr Met Gln Leu Lys Ser Leu Thr Ser
                85                  90                  95

Glu Asp Ser Ala Val Tyr Tyr Cys Ala Arg Glu Val Asp Tyr Trp Gly
            100                 105                 110

Gln Glu Thr Thr Val Thr Val Ser Gly Gly Gly Ser Gly Gly
        115                 120                 125

Gly Gly Ser Gly Gly Gly Ser Asp Ile Glu Leu Thr Gln Ser Pro
    130                 135                 140

Ala Ser Leu Ala Val Ser Leu Gly Gln Arg Ala Thr Ile Ser Tyr Arg
145                 150                 155                 160

Ala Ser Lys Ser Val Ser Thr Ser Gly Tyr Ser Tyr Met His Trp Asn
                165                 170                 175

Gln Gln Lys Pro Gly Gln Pro Pro Arg Leu Leu Ile Tyr Leu Val Ser
            180                 185                 190

Asn Leu Glu Ser Gly Val Pro Ala Arg Phe Ser Gly Ser Gly Ser Gly
        195                 200                 205

Thr Asp Phe Thr Leu Asn Ile His Pro Val Glu Glu Asp Ala Ala
    210                 215                 220

Thr Tyr Tyr Cys Gln His Ile Arg Glu Leu Thr Arg Ser Glu Gly Thr
225                 230                 235                 240

Lys Leu Glu Ile Lys Arg Ala Ala Ala Gly Ala Pro Val Pro Tyr
                245                 250                 255

<210> SEQ ID NO 27
<211> LENGTH: 238
<212> TYPE: PRT
<213> ORGANISM: Unknown
<220> FEATURE:
<223> OTHER INFORMATION: HuCY

<400> SEQUENCE: 27

Gln Val Gln Leu Val Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ala Pro Gly Lys Ser Leu Glu Trp Ile
        35                  40                  45

Gly Asn Ile Asp Pro Tyr Tyr Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80
```

```
Met Gln Leu Lys Ser Leu Arg Ser Glu Asp Thr Ala Val Tyr Tyr Cys
                85                  90                  95

Ala Arg Glu Val Asp Tyr Trp Gly Gln Gly Thr Thr Val Thr Val Ser
            100                 105                 110

Ser Gly Gly Gly Gly Ser Gly Gly Gly Ser Gly Gly Gly Gly Ser
        115                 120                 125

Asp Ile Val Leu Thr Gln Ser Pro Ala Ser Leu Ala Val Ser Leu Gly
        130                 135                 140

Glu Arg Ala Thr Ile Ser Cys Arg Ala Ser Lys Ser Val Ser Thr Ser
145                 150                 155                 160

Gly Tyr Ser Tyr Met His Trp Tyr Gln Gln Lys Pro Gly Gln Pro Pro
                165                 170                 175

Arg Leu Leu Ile Tyr Leu Val Ser Asn Leu Glu Ser Gly Val Pro Asp
            180                 185                 190

Arg Phe Ser Gly Ser Gly Ser Gly Thr Asp Phe Thr Leu Thr Ile Ser
        195                 200                 205

Ser Val Glu Ala Glu Asp Val Ala Val Tyr Tyr Cys Gln His Ile Arg
    210                 215                 220

Glu Leu Thr Arg Ser Glu Gly Thr Lys Leu Glu Ile Lys Arg
225                 230                 235

<210> SEQ ID NO 28
<211> LENGTH: 238
<212> TYPE: PRT
<213> ORGANISM: Unknown
<220> FEATURE:
<223> OTHER INFORMATION: var3

<400> SEQUENCE: 28

Gln Val Gln Leu Val Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ala Pro Gly Lys Gly Leu Glu Trp Ile
        35                  40                  45

Gly Asn Ile Asp Pro Tyr Tyr Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Arg Ser Glu Asp Thr Ala Val Tyr Tyr Cys
                85                  90                  95

Ala Arg Glu Val Asp Tyr Trp Gly Gln Gly Thr Thr Val Thr Val Ser
            100                 105                 110

Ser Gly Gly Gly Gly Ser Gly Gly Gly Ser Gly Gly Gly Gly Ser
        115                 120                 125

Asp Ile Val Leu Thr Gln Ser Pro Ala Ser Leu Ala Val Ser Leu Gly
        130                 135                 140

Glu Arg Ala Thr Ile Ser Cys Arg Ala Ser Lys Ser Val Ser Thr Ser
145                 150                 155                 160

Gly Tyr Ser Tyr Met His Trp Tyr Gln Gln Lys Pro Gly Gln Pro Pro
                165                 170                 175

Arg Leu Leu Ile Tyr Leu Val Ser Asn Leu Glu Ser Gly Val Pro Asp
            180                 185                 190

Arg Phe Ser Gly Ser Gly Ser Gly Thr Asp Phe Thr Leu Thr Ile Ser
        195                 200                 205

Ser Val Glu Ala Glu Asp Val Ala Val Tyr Tyr Cys Gln His Ile Arg
```

```
                    210                 215                 220
Glu Leu Thr Arg Ser Glu Gly Thr Lys Leu Glu Ile Lys Arg
225                 230                 235

<210> SEQ ID NO 29
<211> LENGTH: 238
<212> TYPE: PRT
<213> ORGANISM: Unknown
<220> FEATURE:
<223> OTHER INFORMATION: var4

<400> SEQUENCE: 29

Gln Val Gln Leu Val Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Asn Met Asn Trp Val Lys Gln Ala Pro Gly Lys Gly Leu Glu Trp Ile
            35                  40                  45

Gly Asn Ile Asp Pro Tyr Tyr Gly Gly Thr Thr Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Lys Ser Leu Arg Ser Glu Asp Thr Ala Val Tyr Tyr Cys
                85                  90                  95

Ala Arg Glu Val Asp Tyr Trp Gly Gln Gly Thr Thr Val Thr Val Ser
                100                 105                 110

Ser Gly Gly Gly Ser Gly Gly Gly Ser Gly Gly Gly Ser
            115                 120                 125

Asp Ile Val Leu Thr Gln Ser Pro Ala Ser Leu Ala Val Ser Leu Gly
        130                 135                 140

Glu Arg Ala Thr Ile Ser Cys Arg Ala Ser Lys Ser Val Ser Thr Ser
145                 150                 155                 160

Gly Tyr Ser Tyr Met His Trp Tyr Gln Gln Lys Pro Gly Gln Pro Pro
                165                 170                 175

Arg Leu Leu Ile Tyr Leu Val Ser Asp Leu Glu Asp Gly Val Pro Asp
            180                 185                 190

Arg Phe Ser Gly Ser Gly Ser Gly Thr Asp Phe Thr Leu Thr Ile Ser
        195                 200                 205

Ser Val Glu Ala Glu Asp Val Ala Val Tyr Tyr Cys Gln His Ile Arg
        210                 215                 220

Glu Leu Thr Arg Ser Glu Gly Thr Lys Leu Glu Ile Lys Arg
225                 230                 235
```